(12) United States Patent
Brennan et al.

(10) Patent No.: US 7,919,577 B2
(45) Date of Patent: Apr. 5, 2011

(54) ADRENOCORTICOTROPIC HORMONE ANALOGS AND RELATED METHODS

(75) Inventors: Miles B. Brennan, Denver, CO (US); Jessica L Costa, Auckland (NZ); Robert M. Dores, Littleton, CO (US); Ute H. Hochgeschwender, Durham, NC (US); Carrie Haskell-Luevano, Archer, FL (US)

(73) Assignees: Colorado Seminary, Denver, CO (US); Oklahoma Medical Research Foundation, Oklahoma City, OK (US); The University of Florida Research Foundation, Inc., Gainesville, FL (US)

( * ) Notice: Subject to any disclaimer, the term of this patent is extended or adjusted under 35 U.S.C. 154(b) by 170 days.

(21) Appl. No.: 11/666,485

(22) PCT Filed: Oct. 27, 2005

(86) PCT No.: PCT/US2005/038789
§ 371 (c)(1),
(2), (4) Date: Apr. 30, 2008

(87) PCT Pub. No.: WO2006/052468
PCT Pub. Date: May 18, 2006

(65) Prior Publication Data
US 2008/0207518 A1 Aug. 28, 2008

Related U.S. Application Data

(60) Provisional application No. 60/622,436, filed on Oct. 27, 2004.

(51) Int. Cl.
*A61K 38/35* (2006.01)
(52) U.S. Cl. .............................. 530/306; 514/12; 514/13
(58) Field of Classification Search ........................ None
See application file for complete search history.

(56) References Cited

U.S. PATENT DOCUMENTS 6,333,031 B1 * 12/2001 Olsson et al. ................. 424/93.7
2003/0195147 A1 * 10/2003 Pillutla et al. .................... 514/12

OTHER PUBLICATIONS

Costa et al. "Mutational analysis of evolutionarily conserved ACTH residues," Gen. Compar. Endocrin. 2004, 136, 12-16.*

Miller et al. "The Medical Treatment of Cushing's Syndrome," Endo. Rev., 1993, 14, 443-458.*
Lindsay et al. "The hypothalamic-pituitary-adrenal axis in pregnancy: challenges in disease detection and treatment.," Endo. Rev., 2005, 26, 775-799.*
Costa, et al., Mutational analysis of evolutionarily conserved ACTH residues, Gen. Comp. Endocrin. 2004, vol. 136, pp. 12-16, entire document, © 2003 Elsevier Inc.
Miller et al., The Medical Treatment of Cushing's Syndrome, Endo. Rev. 1993, vol. 14, No. 4, pp. 443-458, Sections 1-IV, © 1993 by the Endocrine Society.
Lindsay et al., The Hypothalmic-Pituitary-Adrenal Axis in Pregnancy: Challenges in Disease Detection and Treatment. Endo. Rev. 2005, vol. 26, No. 6, pp. 775-799, Especially Section III E, © 2005 by the Endocrine Society.
Baumann, G., et al, "Prolonged corticotropic action of synthetic human ACTH in man", Journ. Clin. Endocr. Metab., 1976, 42:160-63.
Hofmann, K. et al., "Correlation of adrenocorticotropic activity of ACTH analogs with degree of binding to an adrenal cortical particulate preparation", PNAS, 1970, 67:829-836.
Szporny, L., et al, "Biological activity of synthetic 1-39 human corticotropin", Nature, 1968, 218:1169-70.
vanRijzingen, I., et al, "The ACTH(4-9) analog ORG 2766 and recovery after brain damage in animal models—a review", Behav. Brain Res., 1996, 75:1-15.
Zhu, Q et al., "Isolation and mode of action of rabbit corticostatic (antiadrenocorticotropin) peptides" Endocrinology, 1992, 130:1413-1423.

* cited by examiner

*Primary Examiner* — Christina Bradley
(74) *Attorney, Agent, or Firm* — Brinks Hofer Gilson; Alan F. Feeney; Pam C. Ball

(57) ABSTRACT

ACTH analog compounds of the present invention include compounds comprising an ACTH peptide sequence with one or more structural modifications that can have one or more of the following preferred ACTH analog biological functions: (1) reduction of corticosteroid secretion by adrenal membrane in the presence of the ACTH analog compared to unmodified ACTH, (2) reduction of corticosteroid secretion by adrenal membrane in the presence of endogenous ACTH and (3) increased MC-2R binding affinity with reduced activation of the MC-2R receptor compared to unmodified ACTH binding to the MC-2R melanocortin. The ACTH analog compounds of the present invention are therefore useful for treatment or prevention of diseases and disorders related to ACTH, ACTH receptors or corticosteroid secretion, such as premature labor and Cushing's Disease.

36 Claims, 5 Drawing Sheets

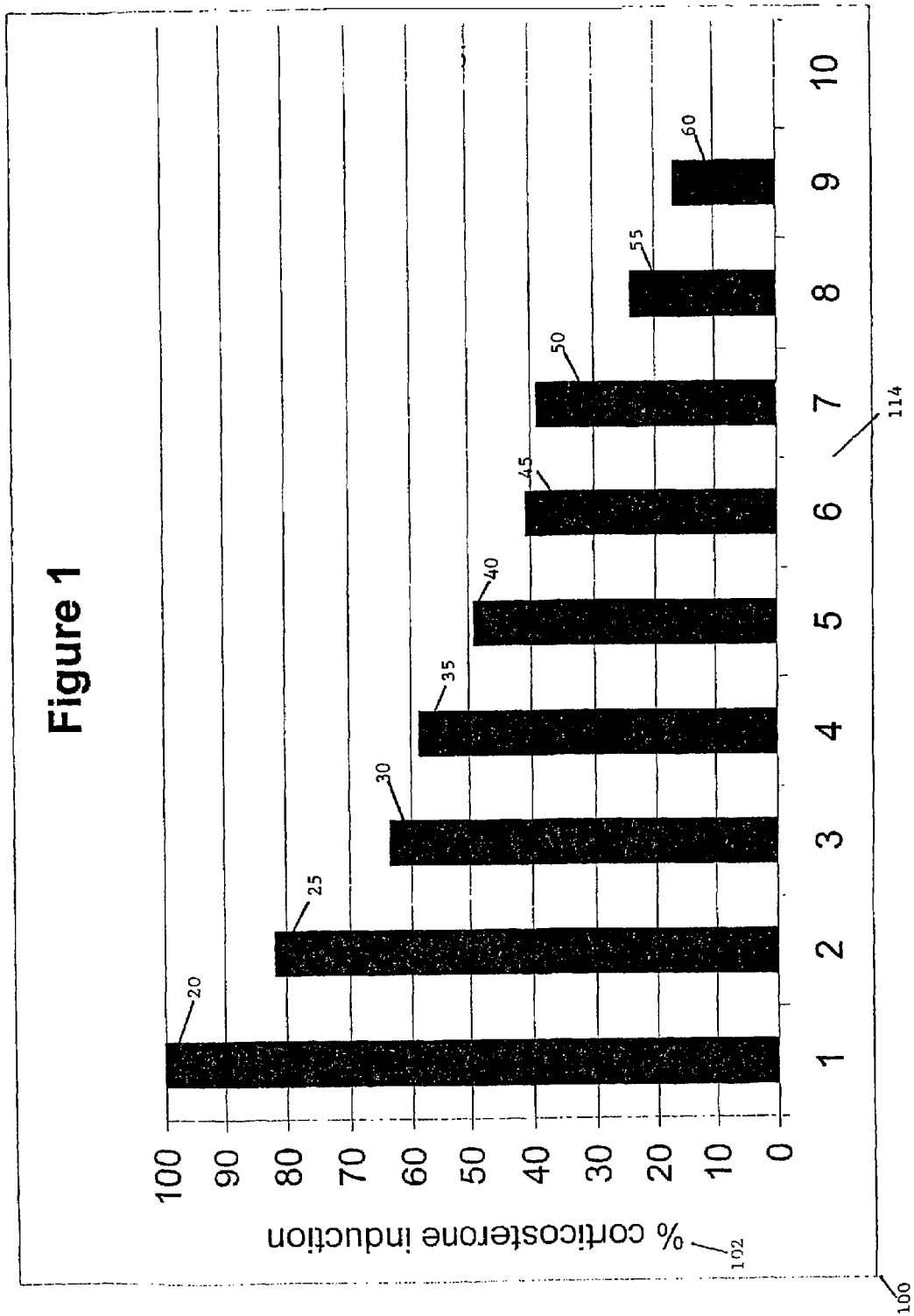

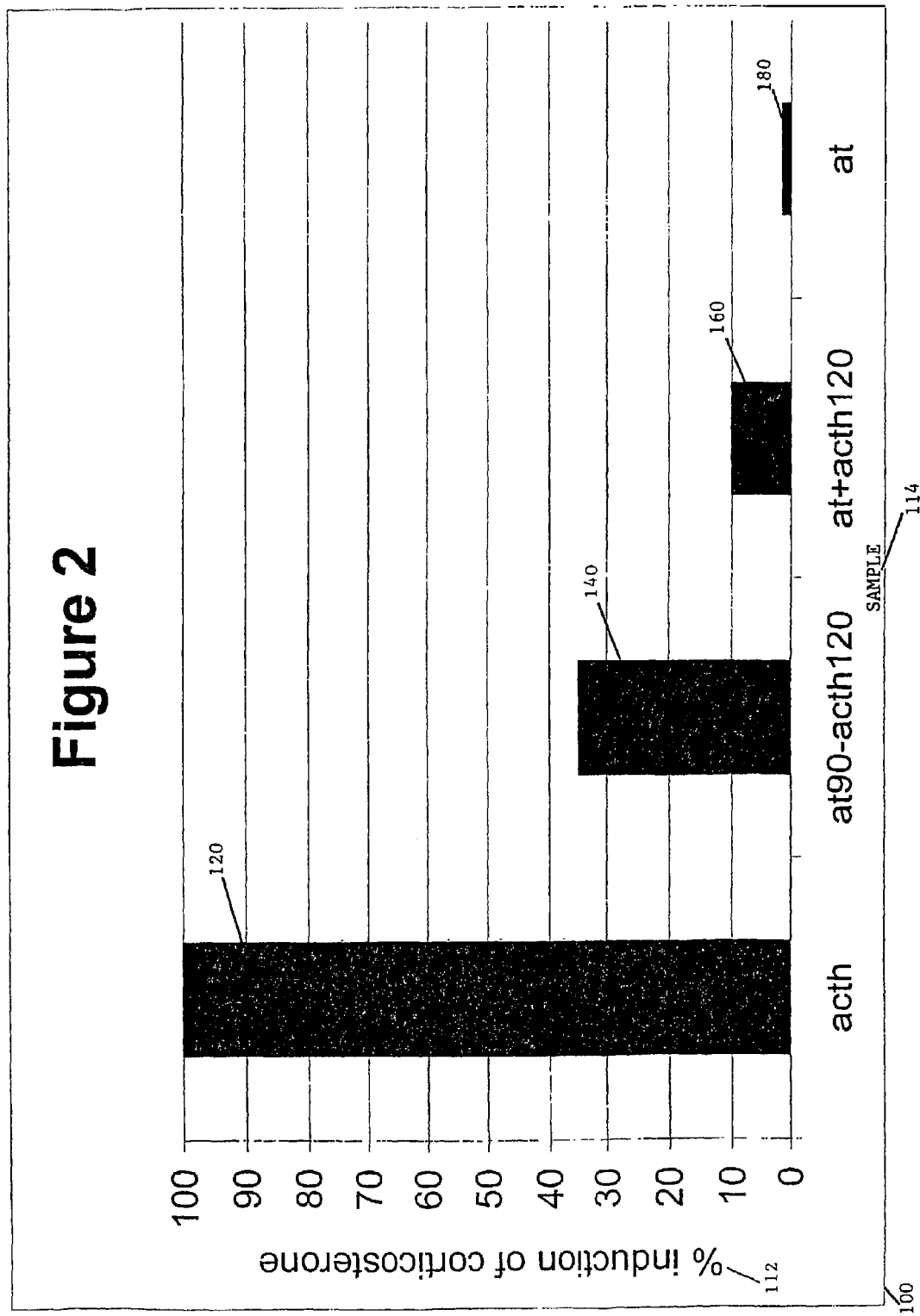

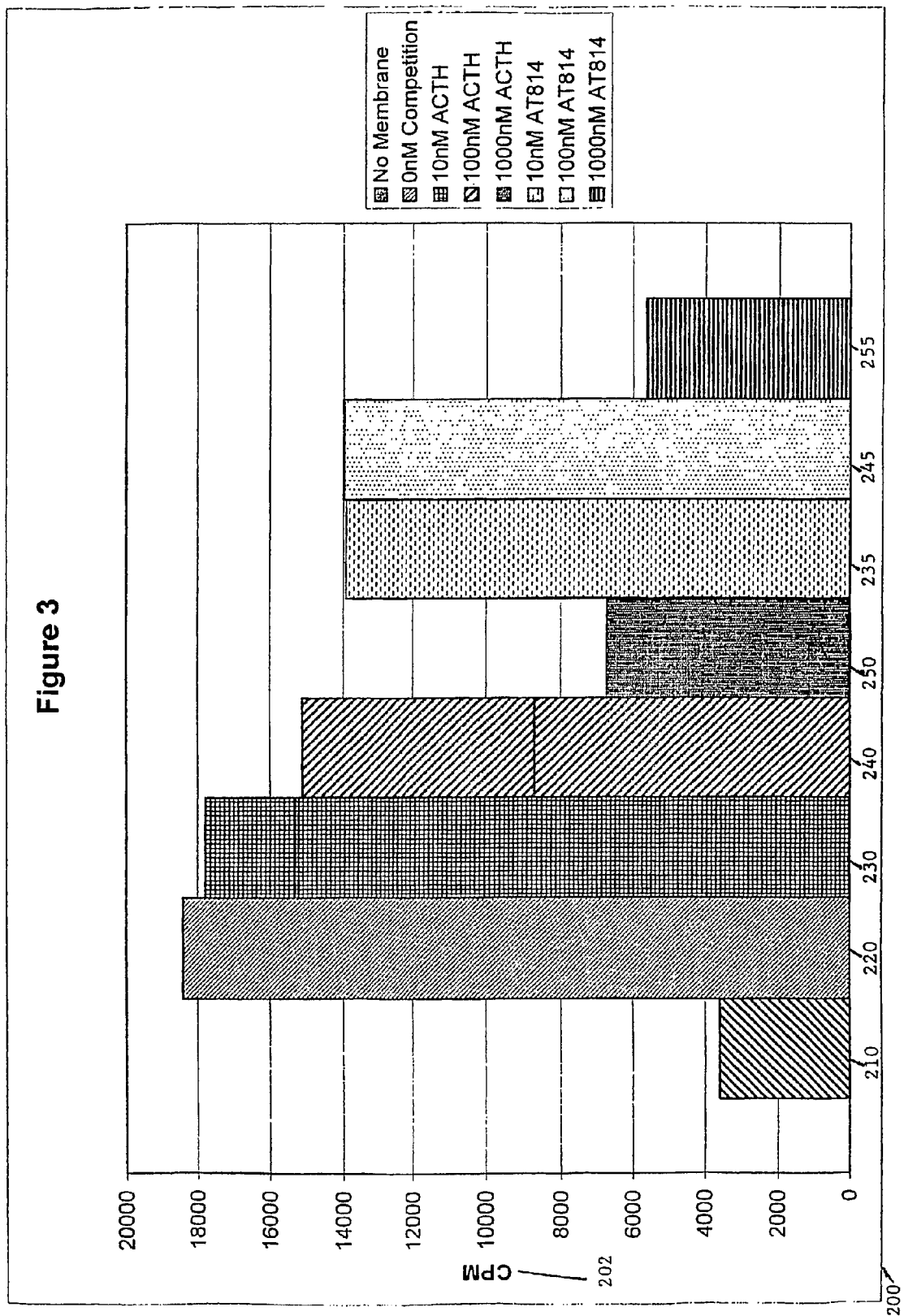

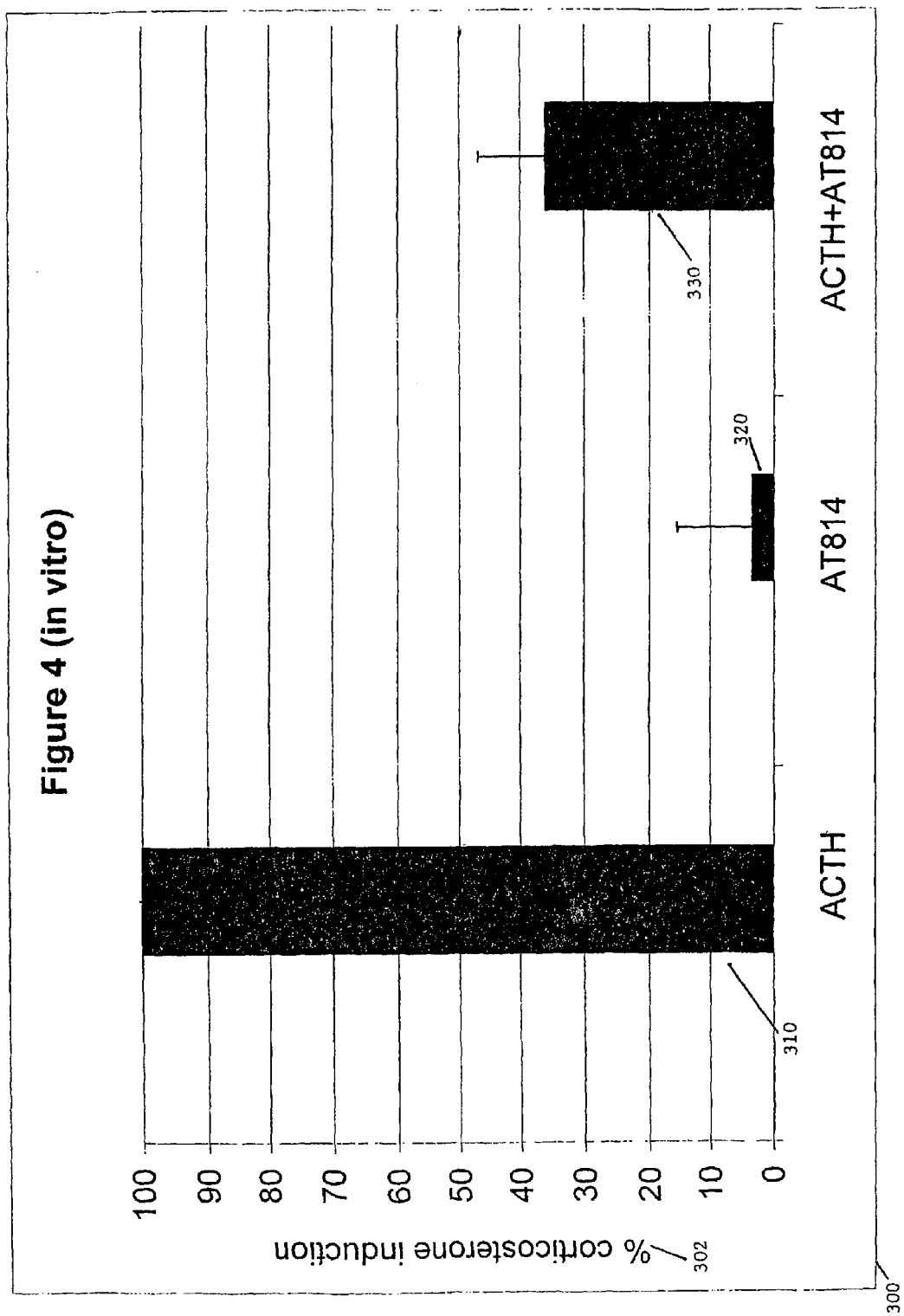

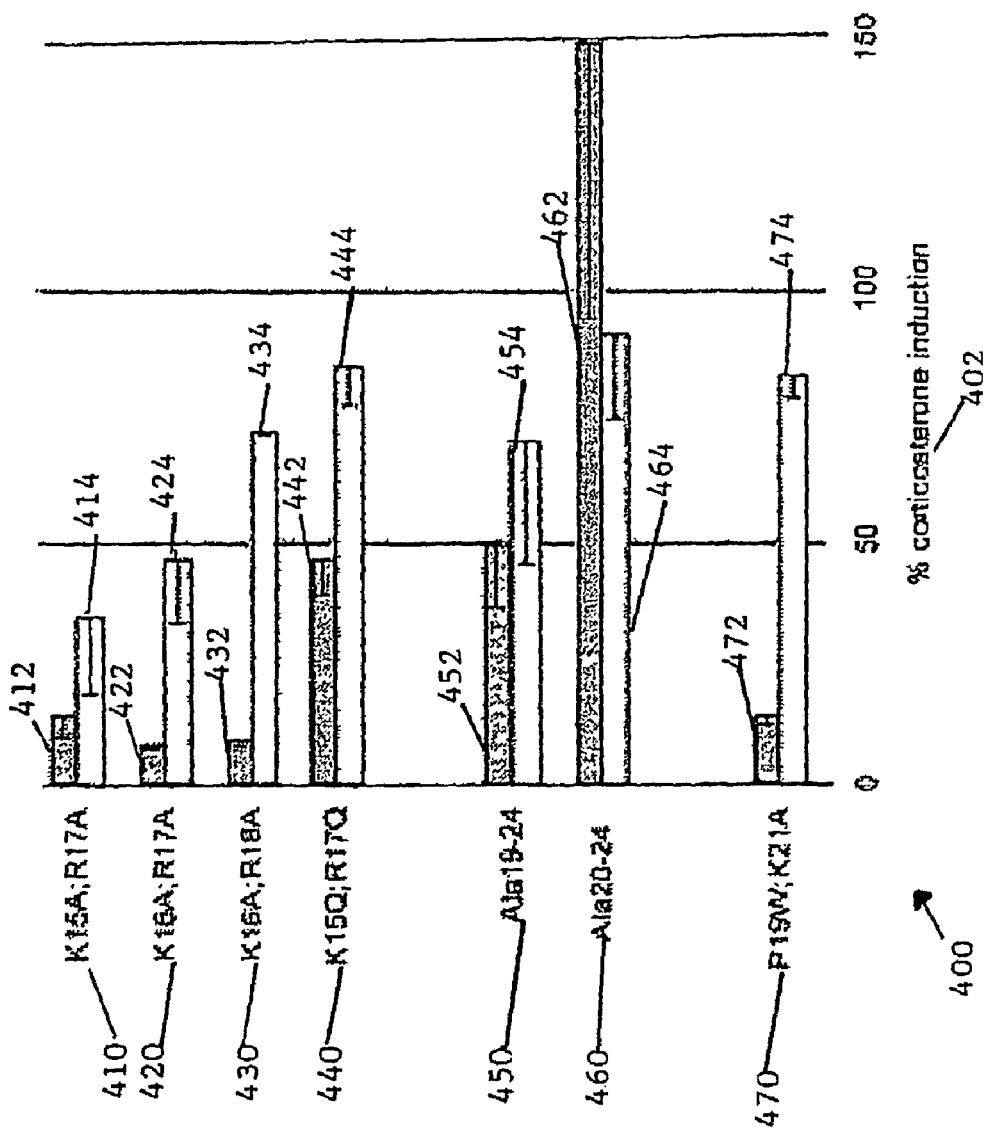

SEQUENCE LISTING

<160> NUMBER OF SEQ ID NOS: 22

<210> SEQ ID NO 1
<211> LENGTH: 39
<212> TYPE: PRT
<213> ORGANISM: Homo sapiens

<400> SEQUENCE: 1

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Ser Ala
            20                  25                  30

Glu Ala Phe Pro Leu Glu Phe
        35

<210> SEQ ID NO 2
<211> LENGTH: 24
<212> TYPE: PRT
<213> ORGANISM: Homo sapiens

<400> SEQUENCE: 2

Ser Tyr Ser Met Glu His Phe Arg Trp Gly Lys Pro Val Gly Lys Lys
1               5                   10                  15

Arg Arg Pro Val Lys Val Tyr Pro
            20

<210> SEQ ID NO 3
<211> LENGTH: 13
<212> TYPE: PRT
<213> ORGANISM: Homo sapiens

<400> SEQUENCE: 3

Ser Tyr Ser Met Glu His Phe Arg Trp Gly Lys Pro Val
1               5                   10

<210> SEQ ID NO 4
<211> LENGTH: 4
<212> TYPE: PRT
<213> ORGANISM: Homo sapiens

<400> SEQUENCE: 4

His Phe Arg Trp
1

<210> SEQ ID NO 5
<211> LENGTH: 4
<212> TYPE: PRT
<213> ORGANISM: Homo sapiens

<400> SEQUENCE: 5

Lys Lys Arg Arg
1

<210> SEQ ID NO 6
<211> LENGTH: 4
<212> TYPE: PRT
<213> ORGANISM: Artificial Sequence
<220> FEATURE:
<223> OTHER INFORMATION: (AA15-18) portion of the ACTH analog

<400> SEQUENCE: 6

Lys Arg Ala Ala
1

```
<210> SEQ ID NO 7
<211> LENGTH: 4
<212> TYPE: PRT
<213> ORGANISM: Artificial Sequence
<220> FEATURE:
<223> OTHER INFORMATION: (AA15-18) portion of the ACTH analog

<400> SEQUENCE: 7

Ala Lys Ala Arg
1

<210> SEQ ID NO 8
<211> LENGTH: 4
<212> TYPE: PRT
<213> ORGANISM: Artificial Sequence
<220> FEATURE:
<223> OTHER INFORMATION: (AA15-18) portion of the ACTH analog

<400> SEQUENCE: 8

Lys Ala Ala Arg
1

<210> SEQ ID NO 9
<211> LENGTH: 4
<212> TYPE: PRT
<213> ORGANISM: Artificial Sequence
<220> FEATURE:
<223> OTHER INFORMATION: (AA15-18) portion of the ACTH analog

<400> SEQUENCE: 9

Lys Ala Arg Ala
1

<210> SEQ ID NO 10
<211> LENGTH: 4
<212> TYPE: PRT
<213> ORGANISM: Artificial Sequence
<220> FEATURE:
<223> OTHER INFORMATION: (AA15-18) portion of the ACTH analog

<400> SEQUENCE: 10

Gln Lys Gln Arg
1

<210> SEQ ID NO 11
<211> LENGTH: 4
<212> TYPE: PRT
<213> ORGANISM: Artificial Sequence
<220> FEATURE:
<223> OTHER INFORMATION: (AA15-18) portion  of the ACTH analog

<400> SEQUENCE: 11

Ala Ala Ala Ala
1

<210> SEQ ID NO 12
<211> LENGTH: 6
<212> TYPE: PRT
<213> ORGANISM: Artificial Sequence
<220> FEATURE:
<223> OTHER INFORMATION: (AA14)-(AA15-18)-(AA19) portion of the ACTH
      analog

<400> SEQUENCE: 12

Gly Lys Arg Ala Ala Trp
1               5
```

-continued

```
<210> SEQ ID NO 13
<211> LENGTH: 6
<212> TYPE: PRT
<213> ORGANISM: Artificial Sequence
<220> FEATURE:
<223> OTHER INFORMATION: (AA14)-(AA15-18)-(AA19) portion of the ACTH
      analog

<400> SEQUENCE: 13

Gly Ala Lys Ala Arg Pro
1               5

<210> SEQ ID NO 14
<211> LENGTH: 6
<212> TYPE: PRT
<213> ORGANISM: Artificial Sequence
<220> FEATURE:
<223> OTHER INFORMATION: (AA14)-(AA15-18)-(AA19) portion of the ACTH
      analog

<400> SEQUENCE: 14

Gly Lys Ala Ala Arg Pro
1               5

<210> SEQ ID NO 15
<211> LENGTH: 6
<212> TYPE: PRT
<213> ORGANISM: Artificial Sequence
<220> FEATURE:
<223> OTHER INFORMATION: (AA14)-(AA15-18)-(AA19) portion of the ACTH
      analog

<400> SEQUENCE: 15

Gly Lys Ala Arg Ala Pro
1               5

<210> SEQ ID NO 16
<211> LENGTH: 6
<212> TYPE: PRT
<213> ORGANISM: Artificial Sequence
<220> FEATURE:
<223> OTHER INFORMATION: (AA14)-(AA15-18)-(AA19) portion of the ACTH
      analog

<400> SEQUENCE: 16

Gly Gln Lys Gln Arg Pro
1               5

<210> SEQ ID NO 17
<211> LENGTH: 6
<212> TYPE: PRT
<213> ORGANISM: Artificial Sequence
<220> FEATURE:
<223> OTHER INFORMATION: (AA14)-(AA15-18)-(AA19) portion of the ACTH
      analog

<400> SEQUENCE: 17

Gly Lys Arg Ala Ala Pro
1               5

<210> SEQ ID NO 18
<211> LENGTH: 5
<212> TYPE: PRT
<213> ORGANISM: Homo sapiens

<400> SEQUENCE: 18

Val Lys Val Tyr Pro
1               5
```

```
<210> SEQ ID NO 19
<211> LENGTH: 5
<212> TYPE: PRT
<213> ORGANISM: Artificial Sequence
<220> FEATURE:
<223> OTHER INFORMATION: (AA20-24) portion of the ACTH analog

<400> SEQUENCE: 19

Ala Ala Ala Ala Ala
1               5

<210> SEQ ID NO 20
<211> LENGTH: 24
<212> TYPE: PRT
<213> ORGANISM: Artificial Sequence
<220> FEATURE:
<223> OTHER INFORMATION: ACTH analog

<400> SEQUENCE: 20

Ser Tyr Ser Met Glu His Phe Arg Trp Gly Lys Pro Val Gly Lys Arg
1               5                   10                  15

Ala Ala Trp Val Lys Val Tyr Pro
            20

<210> SEQ ID NO 21
<211> LENGTH: 15
<212> TYPE: PRT
<213> ORGANISM: Homo sapiens

<400> SEQUENCE: 21

Asn Gly Ala Glu Asp Glu Ser Ala Glu Ala Phe Pro Leu Glu Phe
1               5                   10                  15

<210> SEQ ID NO 22
<211> LENGTH: 39
<212> TYPE: PRT
<213> ORGANISM: Artificial Sequence
<220> FEATURE:
<223> OTHER INFORMATION: analog of ACTH
<220> FEATURE:
<221> NAME/KEY: MISC_FEATURE
<222> LOCATION: (16)..(16)
<223> OTHER INFORMATION: Xaa = Lys, Arg, Gly, Val, Leu, Ile, Nle, Gln,
      Asn, Glu, Asp or an amino acid with an alkyl side chain
<220> FEATURE:
<221> NAME/KEY: MISC_FEATURE
<222> LOCATION: (17)..(17)
<223> OTHER INFORMATION: Xaa = Lys, Arg, Ala, Gly, Val, Leu, Ile, Nle,
      Asn, Glu, Asp or an amino acid with an alkyl side chain
<220> FEATURE:
<221> NAME/KEY: MISC_FEATURE
<222> LOCATION: (18)..(18)
<223> OTHER INFORMATION: Xaa = Lys, Arg, Ala, Gly, Val, Leu, Ile, Nle,
      Gln, Asn, Glu, Asp or an amino acid with an alkyl side chain
<220> FEATURE:
<221> NAME/KEY: MISC_FEATURE
<222> LOCATION: (19)..(19)
<223> OTHER INFORMATION: Xaa = Pro or Trp

<400> SEQUENCE: 22

Ser Tyr Ser Met Glu His Phe Arg Trp Gly Lys Pro Val Gly Lys Xaa
1               5                   10                  15

Xaa Xaa Xaa Val Lys Val Tyr Pro Asn Gly Ala Glu Asp Glu Ser Ala
            20                  25                  30

Glu Ala Phe Pro Leu Glu Phe
            35
```

ADRENOCORTICOTROPIC HORMONE ANALOGS AND RELATED METHODS

CROSS REFERENCE TO RELATED APPLICATIONS

This application is the national phase under 35 U.S.C. §371 of PCT International Application No. PCT/US05/38789, which has an International filing date of Oct. 27, 2005, which designated the United States of America and is incorporated herein by reference in its entirety, and which in turn claims the benefit of U.S. Provisional Patent Application Ser. No. 60/622,436 entitled "Compositions and Methods for the Treatment of Premature Labor, Cushing's Syndrome and Related Disorders," filed Oct. 27, 2004, the entire contents of both applications are incorporated herein by reference.

GOVERNMENT SUPPORT

The subject matter of this application has been supported by a research grant from the National Institutes of Health (Grant Number NIH: DK50870) and a grant from the National Science Foundation (Grant Number NSF IBN-0132210). Accordingly, the government may have certain rights in this invention.

TECHNICAL FIELD

The present invention relates to ACTH analog compounds, as well as related pharmaceutical compositions and methods of treatment.

BACKGROUND

Corticotropin, also known as adrenocorticotropic hormone (ACTH) is a primary hormone secreted by the pituitary gland, that is believed to be a mediator in the production of a variety of vital growth and physiological control steroids. ACTH stimulates the adrenal cortex. More specifically, it stimulates secretion of glucocorticoids such as cortisol in humans (or corticosterone in rodents), and has little control over secretion of aldosterone, the other major steroid hormone from the adrenal cortex. ACTH binds to the MC-2R adrenocorticotropic hormone receptor expressed in the adrenal gland.

ACTH is secreted from the anterior pituitary in response to corticotropin-releasing hormone (CRH) from the hypothalamus. Within the pituitary gland, ACTH is derived from a large precursor molecule pro-opiomelanocortin (POMC) that is cleaved by the action of specific peptidase enzymes. The effects of ACTH on steroid synthesis can include an increase cholesterol esterase, the transport of cholesterol to and across the mitochondrial membrane, cholesterol binding to P450SCC and, hence, an increase in pregnenolone production (see Nussey, S, and S. Whitehead, Endocrinology: An Integrated Approach, BIOS Scientific Publishers Ltd. (2001)). Subsequent actions can include the induction of steroidogenic enzymes and conspicuous structural changes characterized by hypervascularization, cellular hypertrophy and hyperplasia. This is particularly notable in conditions where excess ACTH can be undesirably secreted over prolonged periods of time.

The steroid glucocorticoid is produced by adrenal fasciculata-reticula cells in the adrenal glands, and is secreted in response to an increase in the level of plasma adrenocorticotropic hormone (ACTH). Glucocorticoids are involved in carbohydrate, protein, and fat metabolism, have been shown to have anti-inflammatory properties, and are hypersecreted during stress. In excess, glucocorticoids have been shown to damage the hippocampus, a region of the limbic system of the brain that is critical to cognitive functions such as learning and memory. See, e.g., Sapolsky, R. M., Ann. N.Y. Acad. Sci. 746:294 (1994); and McEwen, B. S., Ann. N.Y. Acad. Sci. 746:134 (1994). Furthermore, glucocorticoid neurotoxicity and neuroendangerment has been shown to be critical in neural development and aging as well as in neurological diseases related to hippocampal damage. See, e.g., deKloet, E. R., et al., Ann. N.Y. Acad. Sci. 746:8 (1994)

Corticosteroids are steroid hormones related structurally to cholesterol. These hormones are synthesized in the adrenal cortex and include the glucocorticoids (e.g. corticosteroids), the mineralocorticoids (e.g. aldosterone) as well as weak androgens and estrogens. The adrenal function, like that of the thyroid gland, is under the control of the hypothalamus (HPT) and the pituitary (PIT). When corticosteroids (the naturally-occurring glucocorticoid) levels drop below a setpoint, the hypothalamus releases CRH (corticotropin releasing hormone) which stimulates adrenocorticotropic hormone (ACTH) release from the pituitary. ACTH is a tropic hormone which stimulates the synthesis and secretion of corticosteroid (it has minimal effects on aldosterone synthesis/secretion), and the growth of the adrenal gland.

There is a need for compounds that bind to ACTH receptors with reduced activation of corticosteroid secretion, for example to treat ACTH-related conditions including: Cushing's Syndrome, impaired immune response as a result of hypersecretion of corticosteroid, and certain adrenal-related causes of premature labor.

Cushing's syndrome is a disorder resulting from increased adrenocortical secretion of corticosteroid. Hyperfunction of the adrenal cortex may be ACTH-dependent or it may be independent of ACTH regulation, e.g. production of corticosteroid by an adrenocortical adenoma or carcinoma. A common cause of Cushing's syndrome is excessive production of ACTH by the pituitary gland. This elevated level of ACTH in the bloodstream typically is produced by a pituitary adenoma (Cushing's disease), but in rare instances has a different etiology. Cushing's syndrome resulting from the production of ACTH in a location other than the pituitary gland is known as ectopic Cushing's syndrome. Examples of ectopic sites include thymoma, medullary carcinoma of the thyroid, pheochromocytoma, islet cell tumors of the pancreas and oat cell carcinoma of the lung. The overwhelming majority of Cushing's syndrome cases in humans, however, trace their etiology to a pituitary adenoma. Symptoms of Cushing's syndrome include weight gain, central obesity, steroid hypersecretion, elevated urinary cortisol excretion, moon face, weakness, fatigue, backache, headache, impotence, mental status changes, muscle atrophy, and increased thirst and urination compared to mammals not suffering from this disease. Diagnosis and treatment of Cushing's syndrome remains a challenge (see Oldfield, E. W. et al., N. Engl. J. Med., 325:897-905 (1991); Findling, J. W. et al., "Diagnosis and differential diagnosis of Cushing's syndrome," Endocrinol. Metab. Clin. North Am., 30:729-47 (2001); Orth, D. N., "Cushing's syndrome," N Engl J. Med., 332:791-803 (1995)). No medical therapies are currently available for Cushing's syndrome. In experienced specialized centers, surgical resection of ACTH-secreting pituitary microadenomas offers an overall cure rate of about 70-80%, but for macroadenomas cure rates only approximate 30%, and the extensive surgical resection required portends significant risk to surrounding normal pituitary tissue, leading to partial or total hypopituitarism in about 80% of cases (Simmons, N. E. et al., "Serum Cortisol response to transphenoidal surgery for Cushing disease," J. Neurosurg., 95:1-8 (2001); Mampalam, T. J. et al., "Transsphenoidal microsurgery for Cushing's disease: A report of 216 cases," Ann. Intern. Med., 109:487-93 (1988); and Trainer, P. J. et al., "Transsphenoidal resection in Cushing's disease: undetectable serum cortisol as the definition of successful treatment," Clin. Endocrinol., 38:73-8 (1993)). Thus, there is also a need for a treatment for Cushing's syndrome where the source of ACTH is a disseminated pituitary tumor or an ectopic source that is effective and does not pose a risk to the patient.

Compounds that bind to ACTH receptors with reduced activation of cortisol secretion can also be used, for example, in treating the hypothalamus-pituitary-adrenal axis for initiation of pre-term labor. Preterm labor occurs in approximately 7-10% of all births and contributes to a substantial proportion of perinatal morbidity and mortality (McCormick, M. C., "The contribution of low birth weight to infant mortality and childhood morbidity," N Engl J. Med., 312:82-90 (1985)). Preventing spontaneous abortion and premature labor, and prolonging gestation in human females, are desirable for many reasons. Gestation is desirably prolonged in order to (i) make more probable a viable live birth, (ii) reduce the incidence of health complications attending a prematurely born child, and (iii) reduce the time period during which a premature infant, even if healthy, must, because of its size and viability, receive extraordinary care. All the factors of (i) live birth, (ii) a healthy child, and (iii) a child that can timely leave the hospital in the custody of its parent(s), desirably impact the happiness and well-being of the parents and relatives. There is also an impact on society from premature births, including a very great societal economic impact in caring for children who are delivered greatly prematurely.

Agriculture and aquaculture can be more cost-effective when the organisms can be raised at high population density. However, among mammals, fowl and fish this frequently results in the over production of adrenal stress hormones with deleterious consequences, including impaired immune function and decreased growth. A method for decreasing the levels of adrenal stress hormones in these or other conditions caused by prolonged stress and resulting in undesirable health changes, e.g. decreased immune function and susceptibility to disease, would also be desirable.

Various compositions and methods can be used to reduce ACTH levels, for example through certain receptors for arginine vasopressin (AVP). U.S. Pat. No. 6,380,155, filed May 3, 2000, relates to the use of certain vasopressin receptor antagonist compositions for the regulation of ACTH release. Compositions to treat ACTH-related conditions that regulate ACTH levels are desirable, such as compositions that can bind to ACTH MC-2R receptors, while reducing or eliminating ACTH-induced corticosteroid production so as to mitigate undesirable conditions associated with elevated ACTH levels.

SUMMARY

Various modified adrenocorticotropic hormone (ACTH) peptides ("ACTH analogs") are provided that reduce or eliminate ACTH-induced corticosteroid secretion compared to unmodified ACTH. Preferably, the ACTH analogs also reduce the secretion of corticosteroid from adrenal membrane in the presence of unmodified ACTH.

The ACTH analog compounds preferably comprise at least amino acids 1-24 of unmodified ACTH, with one or more amino acid substitutions. The ACTH analog compounds can include one or more amino acid substitutions or truncation with respect to the unmodified human ACTH amino acid sequence. Unmodified human ACTH is a polypeptide that has 39 amino acid residues in the following sequence: N-Ser$^1$-Tyr-Ser-Met-Glu$^5$-His-Phe-Arg-Trp-Gly$^{10}$-Lys-Pro-Val-Gly-Lys$^{15}$-Lys-Arg-Arg-Pro-Val$^{20}$-Lys-Val-Tyr-Pro-Asn$^{25}$-Gly-Ala-Glu-Asp-Glu$^{30}$-Ser-Ala-Glu-Ala-Phe$^{35}$-Pro-Leu-Glu-Phe$^{39}$-Ac (SEQ ID NO. 1), where N and Ac represent the amino and carboxy terminal ends, respectively, of the molecule. ACTH analogs can also comprise compounds that include a peptide having one or more substitutions or modifications of the sequence: N-Ser$^1$-Tyr-Ser-Met-Glu$^5$-His-Phe-Arg-Trp-Gly$^{10}$-Lys-Pro-Val-Gly-Lys$^{15}$-Lys-Arg-Arg-Pro-Val$^{20}$-Lys-Val-Tyr-Pro-Ac (SEQ ID NO: 2), where N and Ac represent the amino and carboxy terminal ends, respectively, of the molecule. Preferred ACTH analog compounds include at least amino acid residues 1-19 of hACTH or mACTH, more preferably amino acid residues 1-24 of hACTH or mACTH, with one or more amino acid substitutions.

ACTH analog compounds include compounds comprising the ACTH sequence of SEQ ID NO:1 or SEQ ID NO:2 with one or more structural modifications that result in one or more of the following preferred ACTH analog biological functions: (1) reduction of corticosteroid secretion by adrenal membrane in the presence of the ACTH analog compared to unmodified ACTH, (2) reduction of corticosteroid secretion by adrenal membrane in the presence of endogenous ACTH and (3) increased MC-2R binding affinity with reduced activation of the MC-2R receptor compared to unmodified ACTH. Examples of preferred ACTH amino acid substitutions to form ACTH analog compounds include one or more of the following: (1) substitutions of one or more amino acid residues at positions 1-13 that conserve the amino acids at positions 6-9 and/or promote or preserve MC-2R binding, (2) substitution of one or more amino acid residues at positions 15-18 that prevent or antagonize enzymatic cleavage at these positions, (3) substitution of one or more amino acid residues at positions 15-18 such that the ACTH analog does not comprise adjacent amino acid residues with basic side chains at positions 15-18, (4) substitution or truncation of one or more amino acid residues at positions 20-24 that extend the serum half life of the ACTH analog, (5) substitution of one or more amino acid residues at positions 20-36 that result in an ACTH analog that reduces the corticosteroid secretion of adrenal membrane in the presence of the ACTH analog compound compared to an unmodified ACTH peptide, (6) substitution or preferably truncation of one or more amino acid residues at positions 25-39 that provide ACTH analog compounds with desired release properties, or (7) truncation of amino acid residues 25-39, with the amino acid residue at position 24 forming the carboxy terminus of the molecule.

The ACTH analog compounds preferably bind to ACTH receptors such as the melanocortin 2 receptor (MC-2R) in adrenal membrane. More preferably, the ACTH analog compounds do not activate, or weakly activate, cells expressing MC-2R and inhibit or reduce the action of unmodified endogenous ACTH.

In a first embodiment, various ACTH analog compounds can include one or more amino acid substitutions or truncation with respect to the unmodified human ACTH amino acid sequence. For example, a composition comprising an isolated ACTH analog peptide can include a peptide of SEQ ID NO:2 with at least one of the following amino acid substitutions:

a. the substitution of the Pro residue at position 19 of SEQ ID NO:2 with the amino acid Trp; or b. one or more amino acid substitutions of residues selected from amino acid residues 16 to 18 of SEQ ID NO:2, such that the amino acid residues 16, 17 and 18 of the ACTH analog do not include any two adjacent amino acid residues selected from the group consisting of: Lys and Arg; and the one or more amino acid residues substituted at position 16, 17 or 18 of SEQ ID NO:2 are selected from the group consisting of: Lys, Arg, Gln, Gly, Ala, Val, Leu, Ile and an amino acid analog having an alkyl side chain (such as Nle). Optionally, the ACTH analog peptide can include at least one Ala, Gly, or another amino acid with an alkyl side chain (i.e., Val, Leu, Ile, an amino acid analog comprising an alkyl side chain such as Nle), and at least one Arg residue substituted at any two of the amino acid positions 15, 16, 17 or 18 of SEQ ID NO:2. The ACTH analog can optionally consist essentially of the sequence of SEQ ID NO:2 with the following amino acid substitutions: the Pro residue at position 19 of SEQ ID NO:2 is substituted with the amino acid Trp; the amino acid at position 15 of SEQ ID NO:2 is selected from the group consisting of: Lys, Ala and Gln; and the ACTH analog peptide can comprise one or more amino acid substitutions of residues selected from amino acid residues 16 to 18 of SEQ ID NO:2, such that the amino acid residues 16, 17 and 18 of the ACTH analog do not include any two adjacent amino acid residues selected from the group consisting of: Lys and Arg. Preferably, the ACTH analog peptide includes the amino acid sequence of SEQ ID NO:4 at amino acid residues 6, 7, 8 and 9. The ACTH analog peptide can also include the amino acid sequence of SEQ ID NO:12 at amino acid residues 15-19.

The first embodiment also includes ACTH analogs having the peptide of SEQ ID NO:1 with at least one amino acid substitution, such as substitution of an amino acid residue at position 19, 26, 30 or 36 of SEQ ID NO:1. The ACTH analog peptide can also include the peptide of SEQ ID NO:1 with at least one of the following amino acid substitutions:

a. substitution of the Pro residue at position 19 of SEQ ID NO:1 with the amino acid Trp or b. one or more amino acid substitutions of residues selected from amino acid residues 16 to 18 of SEQ ID NO:1, such that the amino acid residues 16, 17 and 18 of the ACTH analog do not include any two adjacent amino acid residues selected from the group consisting of: Lys and Arg; and the one or more amino acid residues substituted at position 16, 17 or 18 of SEQ ID NO:2 is selected from the group consisting of: Lys, Arg, Gln, Gly, Ala, Val, Leu, Ile and Nle (or another amino acid analog having an alkyl side chain).

Other preferred ACTH analog peptides include modifications of peptides of SEQ ID NO:1 or SEQ ID NO:2 such that the ACTH analog peptide include the amino acid sequence of SEQ ID NO:6 at amino acid residues 15-19. ACTH analog peptides also include truncation of one or more peptides ACTH analog further comprises truncation of amino acid residues 25-39 of SEQ ID NO:1. ACTH analog peptides of SEQ ID NO:20 are particularly preferred.

In some embodiments, the administration of an ACTH analog peptide reduces the ACTH induced production of corticosterone by adrenal membrane in an in vitro Serum Corticosteroid Induction Assay by at least 10%, and preferably up to 100%, compared to the peptide of SEQ ID NO:2. For instance, in a second embodiment, ACTH analogs are modified ACTH peptides that function to reduce corticosteroid secretion by adrenal membrane in the presence of the ACTH analog compared to unmodified ACTH.

In some embodiments, the administration of the ACTH analog peptide in an in vivo Serum Corticosteroid Inhibition Assay reduces ACTH-induced corticosteroid secretion by at least a 10%. In a third embodiment, ACTH analogs are modified ACTH peptides that function to reduce corticosteroid secretion by adrenal membrane in the presence of endogenous ACTH.

In some embodiments, compositions are provided that include an isolated ACTH analog peptide of SEQ ID NO:2 with at least one amino acid substitution, wherein the ACTH analog peptide binds to and displaces a peptide of SEQ ID NO:2 from adrenal membrane. The peptide binding can be measured by an in vitro Serum-Free Adrenal Competitive Binding Assay. For example, in a fourth embodiment, ACTH analogs are modified ACTH peptides that function to bind to adrenal ACTH receptors, such as the MC-2R receptor, preferably with increased MC-2R binding affinity and reduced activation of the MC-2R receptor compared to unmodified ACTH. Preferably, the ACTH analog peptide can bind to and displace a peptide of SEQ ID NO:2 from adrenal membrane, where the peptide binding is measured by an in vitro Serum-free Adrenal Competitive Binding Assay. Most preferably, the ACTH analog peptide binds to the MC-2R adrenal membrane with at least a 2-fold greater affinity than the peptide of SEQ ID NO:2.

In some embodiments, the ACTH analog peptide reduces the ACTH induced production of corticosterone by adrenal membrane in an in vitro Serum-free Adrenal Inhibition Assay. For example, in a fifth embodiment, ACTH analog compounds can reduce corticosteroid induction by unmodified ACTH in explanted tissue in vitro. The ACTH analogs include peptides that reduce the ACTH induced production of corticosterone by adrenal membrane in an in vitro Serum-free Adrenal Inhibition Assay.

In a sixth embodiment, extended half-life ACTH analogs are provided. Extended half-life ACTH analogs can be identified as having a first activity measured by the concentration of serum corticosteroid detected in vivo that is greater than a second activity measured by the serum-free concentration of corticosteroid detected the in vitro activity, where the in vivo activity is measured by the measured by the Serum Adrenal Corticosteroid Inhibition Assay of Example 2 and the in vitro activity is measured by in vitro Serum-Free Adrenal Corticosteroid Inhibition Assay of Example 4.

In a seventh embodiment, methods for screening ACTH analogs that are useful in blocking excess ACTH while maintaining adrenal tone are also provided. Various ACTH analogs can be prepared and administered to a patient to assess in vivo cortisone induction.

In an eighth embodiment, the present disclosure pertains to pharmaceutical compositions comprising ACTH analogs, and the administration thereof to a subject in a manner commensurate with treatment for symptoms associated with an ACTH-related condition. The ACTH analogs described herein can be incorporated in pharmaceutical compositions for treating ACTH-related conditions, such as ACTH overexpression in humans or animals. Methods for producing ACTH analogs and associated pharmaceutical compositions containing the ACTH analogs are also provided. For example, in one aspect, methods for screening a class of ACTH analogs for compounds useful in blocking excess ACTH while maintaining adrenal tone is provided.

The ACTH analog compounds can be useful in treating diseases relating to levels of ACTH, such as conditions responsive to modulation of ACTH receptors (such as MC-2R). Compounds useful for regulating corticosteroid secretion or corticosteroid levels are also provided. The ACTH analog compounds can be administered to treat conditions related to the regulation of ACTH levels, for example to decrease the effects of high levels of ACTH in patients while maintaining a tonic state of adrenal function. The ACTH analog compositions are useful, for example, in treating ACTH-related conditions, such as Cushing's Syndrome, impaired immune response as a result of hypersecretion of corticosteroid, initiation of premature labor (for example, by the hypothalamus-pituitary-adrenal axis), and related conditions. In one aspect, various ACTH analogs are prepared and administered to a patient to assess in vivo cortisone induction. In another aspect, methods for treating veterinary subjects are provided, such as methods for decreasing stress hormones to benefit the health of agricultural and aquacultural species grown at high population densities.

BRIEF DESCRIPTION OF THE DRAWINGS

In the accompanying drawings:

FIG. 1 is a graph showing the levels of corticosterone measured in vivo after injection of various ACTH analog compounds, as compared to the level of corticosterone measured after administering unmodified ACTH.

FIG. 2 is a graph comparing the in vivo corticosterone induced by administration of unmodified ACTH, an ACTH analog in combination with unmodified ACTH, the ACTH analog followed by separate administration of the unmodified ACTH, and the ACTH analog alone.

FIG. 3 is a graph comparing the results of a competitive binding assay for adrenal ACTH receptors for unmodified ACTH and an ACTH analog compound.

FIG. 4 is a graph comparing the in vitro corticosterone induced in explanted adrenal membrane by unmodified ACTH, an ACTH analog in combination with unmodified ACTH, and the ACTH analog alone.

FIG. 5 is a graph comparing the in vivo and in vitro activity of various ACTH agonist compounds in inducing corticosterone, referenced to the activity of unmodified ACTH (i.e., 100%).

DETAILED DESCRIPTION

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

As used herein, the term "unmodified Adrenocorticotropic Hormone" ("unmodified ACTH") means the peptide hormone produced by the anterior pituitary gland that stimulates the adrenal cortex to secrete glucocorticoid hormones, which help cells synthesize glucose through the process of gluconeogenesis, catabolize proteins, mobilize free fatty acids and inhibit inflammation in allergic responses. One such hormone is corticosteroid, which regulates metabolism of carbohydrate, fat, and protein metabolism.

The term "corticosteroid" as used herein includes the human corticosteroid cortisol and the rodent corticosteroid corticosterone.

The term "about" used with reference to a quantity includes variations in the recited quantity that are equivalent to the quantity recited, for instance an amount that is insubstantially different from a recited quantity for an intended purpose or function.

The nomenclature "P(x-y)" as used herein, where P is the name of a polypeptide and x and y are integers, refers to an amino acid sequence consisting of the consecutive amino acids at position (x) to position (y) of the polypeptide called "P". For example, "hACTH(1-24)" refers to the polypeptide of 24 consecutive amino acids consisting of the residues 1 through 24 from the amine terminal end of the human ACTH peptide. Recitation of "mACTH" refers to murine ACTH. Notably, hACTH(1-24) and mACTH(1-24) are identical peptide sequences.

The nomenclature "aXb" where a and b are single-letter abbreviations for amino acids and X is a number, refers to a substitution of the amino acid "a" in the "X" position in the unmodified ACTH peptide with the amino acid "b." For example, "(V26F,E30K)mACTH" refers to a 39 amino acid mouse ACTH molecule that has been modified by substituting a Phe amino acid in place of the Val amino acid at the 26 position from the amino terminus of the molecule, and substituting a Lys amino acid in place of the Glu amino acid at the 30 position from the amino terminus of the molecule. Similarly, the nomenclature "αβχX-Yδεφ" where α, β, χ, δ, ε, and φ represent single-letter abbreviations for amino acids and X and Y are numbers, refers to the substitution of the consecutive amino acids "αβχ" at positions X to Y with amino acids "δεφ."

ACTH analog compounds include compounds comprising the ACTH sequence with one or more structural modifications that provide one or more of the following preferred ACTH analog biological functions: (1) reduction of corticosteroid secretion by adrenal membrane in the presence of the ACTH analog compared to unmodified ACTH, (2) reduction of corticosteroid secretion by adrenal membrane in the presence of endogenous ACTH, (3) increased MC-2R binding affinity accompanied by a reduced activation of the MC-2R receptor compared to unmodified ACTH. The ACTH analog compounds are believed to act by binding to the melanocortin 2 receptor (MC-2R), weakly activating cells expressing MC-2R, and blocking the action of endogenous ACTH on the MC-2R receptor.

Examples of preferred ACTH amino acid substitutions that can be used to form ACTH analog compounds with one or more of the desired functions include: (1) substitutions of one or more amino acid residues at positions 1-13 that conserve the amino acids at positions 6-9 and/or promote or preserve MC-2R binding, (2) substitution of one or more amino acid residues at positions 15-18 that prevent or antagonize enzymatic cleavage at these positions, (3) substitution of one or more amino acid residues at positions 15-18 that are not characterized by adjacent dibasic amino acids, (4) substitution or truncation of one or more amino acid residues at positions 20-24 that extend the serum half life of the ACTH analog, (5) substitution or preferably truncation of one or more amino acid residues at positions 25-39 that provide ACTH analog compounds with desired release properties, or (6) truncation of amino acid residues 25-39, with the amino acid residue at position 24 forming the carboxy terminus of the molecule.

ACTH Analog Compounds

In a first embodiment, various ACTH analog compounds can include one or more amino acid substitutions or truncation with respect to the unmodified human ACTH amino acid sequence. Unmodified human ACTH is a polypeptide that has 39 amino acid residues in the following sequence: N-Ser$^1$-Tyr-Ser-Met-Glu$^5$-His-Phe-Arg-Trp-Gly$^{10}$-Lys-Pro-Val-Gly-Lys$^{15}$-Lys-Arg-Arg-Pro-Val$^{20}$-Lys-Val-Tyr-Pro-Asn$^{25}$-Gly-Ala-Glu-Asp-Glu$^{30}$-Ser-Ala-Glu-Ala-Phe$^{35}$-Pro-Leu-Glu-Phe$^{39}$-Ac (SEQ ID NO: 1) ("hACTH"), where N and Ac represent the amino and carboxy terminal ends, respectively, of the molecule. ACTH(1-24) is conserved in that the ACTH (1-24) is found in many chordates, including both human ACTH(1-24) and has the peptide sequence: N-Ser$^1$-Tyr-Ser-Met-Glu$^5$-His-Phe-Arg-Trp-Gly$^{10}$-Lys-Pro-Val-Gly-Lys$^{15}$-Lys-Arg-Arg-Pro-Val$^{20}$-Lys-Val-Tyr-Pro-Ac (SEQ ID NO: 2) (as well as being identical to the 1-24 portion of murine ACTH ("mACTH(1-24)"), where N and Ac represent the amino and carboxy terminal ends, respectively, of the molecule.

ACTH analog compounds can include at least amino acid residues 1-19, more preferably amino acid residues 1-24, of hACTH (SEQ ID NO:1) with one or more amino acid substitutions. Preferred ACTH analog compounds comprise SEQ ID NO:2 modified by one or more amino acid substitutions. ACTH analog compounds include compounds comprising the ACTH sequence with one or more structural modifications that provide one or more of the following preferred ACTH analog biological functions: (1) reduction of corticosteroid secretion by adrenal membrane in the presence of the ACTH analog compared to unmodified ACTH, (2) reduction of corticosteroid secretion by adrenal membrane in the presence of endogenous ACTH and (3) increased MC-2R binding affinity with reduced activation of the MC-2R receptor compared to unmodified ACTH.

Particularly preferred ACTH analog compounds have one or more of the following amino acid substitutions to the unmodified human ACTH sequence: (1) substitutions of one or more amino acid residues at positions 1-13 that conserve the amino acids at positions 6-9, (2) substitution of one or more amino acid residues at positions 15-18 that prevent or antagonize enzymatic cleavage at these positions, (3) substitution of one or more amino acid residues at positions 15-18 that are not characterized by adjacent dibasic amino acids, (4) substitution or truncation of one or more amino acid residues at positions 20-24 that extend the serum half life of the ACTH analog, and (5) substitution or preferably truncation of one or more amino acid residues at positions 25-39 that provide ACTH analog compounds with extended serum half life compared to unmodified ACTH or compared to other ACTH analog compounds.

The ACTH analog preferably comprises a polypeptide described by the formula (I) below:

N-(AA$^{1-13}$)-(AA$^{14}$)-(AA$^{15-18}$)-(AA$^{19}$)-Ac     (I)

where N- and Ac- indicate the amino terminal end and carboxy end, respectively, of the polypeptide, (AA$^{1-13}$)- indicates a first series of thirteen consecutive amino acids or amino acid analogs, (AA$^{14}$)- represents an amino acid residue attached to the carboxy terminal end of the first series, (AA$^{15-18}$)- indicates a second series of four consecutive amino acids attached at the carboxy terminal end of (AA$^{14}$), (AA$^{19}$)- represents an amino acid residue attached to the carboxy terminal end of the second series.

The ACTH analog of formula (I) preferably further comprises a portion of a larger molecule attached to the carboxy end of the (AA$^{19}$)-Ac portion. The ACTH analog can further include additional amino acids attached to the carboxy end (Ac) of formula (I). Most preferably, ACTH analogs include a total of five additional amino acids attached at the Ac portion of formula (I), with a total of at least 24 amino acids in the ACTH analog.

ACTH analogs can comprise the amino acid sequence of unmodified ACTH corresponding to formula (I), preferably including one or more amino acid substitutions. Additional amino acids or amino acid analogs are preferably attached to the carboxy terminal end of the (AA$^{19}$)- residue of formula (I).

The (AA$^{1-13}$)- portion of formula (I) represents a sequence of thirteen amino acids of formula (II):

-AA$^1$-AA$^2$-AA$^3$-AA$^4$-AA$^5$-AA$^6$-AA$^7$-AA$^8$-AA$^9$-AA$^{10}$-AA$^{11}$-AA$^{12}$-AA$^{13}$-     (II)

having the unmodified ACTH amino acid sequence described in the second row of Table 1, optionally including one or more amino acid substitutions provided in the third row of Table 1. The (AA$^{1-13}$)- portion of unmodified human ACTH has the sequence Ser-Tyr-Ser-Met-Glu-His-Phe-Arg-Trp-Gly-Lys-Pro-Val (SEQ ID NO:3). Preferably, the AA$^6$-AA$^7$-AA$^8$-AA$^9$- portion of formula (II) has the unmodified amino acid sequence His-Phe-Arg-Trp- (SEQ ID NO:4), optionally substituted with one or more (D) amino acid analogs thereof.

TABLE 1

ACTH analog amino acid substitution of (AA$^{1-13}$)

| Residue: | AA$^1$- | AA$^2$- | AA$^3$- | AA$^4$- | AA$^5$- | AA$^6$- | AA$^7$- | AA$^8$- | AA$^9$- | AA$^{10}$ | AA$^{11}$- | M$^{12}$- | AA$^{13}$- |
|---|---|---|---|---|---|---|---|---|---|---|---|---|---|
| Unmodified ACTH Residue: | Ser | Tyr | Ser | Met | Glu | His | Phe | Arg | Trp | Gly | Lys | Pro | Val |
| Optional ACTH analog Amino Acid Substitutions | (D)Ser | (D)Tyr | (D)Ser | (D)Met Nle | (D)Glu Cys Asp | (D)His | (D)Phe (D)-p-iodoPhe (D)-l-naph-Ala | (D)Arg | (D)Trp | Cys Lys Orn Dab Dpr | (D)Lys Gly | (D)Pro | (D)Val |

In Table 1, the designation (D) refers to the (D) enantiomer of the indicated amino acids; Nle refers to the amino acid analog norleucine or another amino acid with an alkyl side chain; Orn refers to ornithine, or another modified amino acid with a similar side chain; Dab refers to 2,4 diaminobutyric acid, or a similar diamino acid; Dpr refers to 2,3 diaminopropionic acid or another diamino acid, (D) p-iodo-Phe refers to steric group such as a p-iodo modified Phe amino acid; and (D)-l-naph-Ala refers to the l-naph-modified (D)-Ala amino acid, or another sterically modified amino acid. ACTH analog compounds that include substitutions to the unmodified (AA$^{1-13}$) portion of the unmodified ACTH preferably include one of the optional ACTH analog Amino Acid residues indicated below a given residue position in Table 1. For example, unmodified ACTH has a Glu residue at the AA$^5$ position, that can optionally be substituted with a (D)-Glu, Cys or Asp residue in forming an ACTH analog. The amino acid sequence of formula (II) can also include one or more amino acid substitutions corresponding to MC-2R binding sequences disclosed by Hruby et al. in U.S. Pat. Nos. 4,485,039; 4,457,864; 4,866,038; 5,731,408; 5,714,576; 5,049,547; 4,918,055; 4,649,191; and 5,674,839, which are incorporated herein by reference.

The (AA$^{14}$)- portion of formula (I) represents an amino acid residue that is preferably Gly or (D) Gly, although other amino acids can be substituted at the $(AA^{14})$- position that preserve desirable biological functions of ACTH analog compounds, such as the reduction of corticosteroid secretion by the ACTH analog compared to ACTH, reduction of corticosteroid secretion by endogenous ACTH and/or MC-2R binding.

The $(AA^{15-18})$- portion of formula (I) represents a sequence of four amino acids of formula (III):

$$-AA^{15}-AA^{16}-AA^{17}-AA^{18}-. \quad (III)$$

The $(AA^{15-18})$- portion of unmodified human ACTH comprises the sequence Lys-Lys-Arg-Arg (SEQ ID NO:5), which includes four adjacent amino acids with basic side chains. Preferably, ACTH analog compounds include substitution of one or more amino acid residues in formula (III) that prevent or antagonize enzyme cleavage at these positions. Also preferably, ACTH analog compounds include substitution of one or more amino acid in formula (III) that are not characterized by adjacent amino acids with basic side chains. $AA^{15}$- and $AA^{16}$- are preferably independently selected from the group consisting of: Lys, Ala, Gly and Val; $AA^{17}$-$AA^{18}$ are preferably independently selected from the group consisting of: Arg, Ala, Gly and Val.

In one aspect, one or more amino acid substitutions of residues $AA^{16}$-$AA^{17}$-$AA^{18}$ of SEQ ID NO:2 or formula (III) are selected such that the amino acid residues 16, 17 and 18 of the ACTH analog do not include any two adjacent amino acid residues selected from the group consisting of: Lys and Arg. In other words, in some ACTH analogs, the amino acids Lys and Arg do not appear adjacent to each other (i.e., an arginine adjacent to a lysine or vice versa) or to themselves (i.e., an arginine adjacent to another arginine, or a lysine adjacent to another lysine) within the $AA^{16}$-$AA^{17}$-$AA^{18}$ portion of the peptide sequence. Instead, one or more of the amino acids within the $AA^{16}$-$AA^{17}$-$AA^{18}$ portion are substituted with any amino acid or amino acid analog other than Lys or Arg that provide one or more of the following preferred ACTH analog biological functions: (1) reduction of corticosteroid secretion by adrenal membrane in the presence of the ACTH analog compared to unmodified ACTH, (2) reduction of corticosteroid secretion by adrenal membrane in the presence of endogenous ACTH and (3) increased MC-2R binding affinity with reduced activation of the MC-2R receptor compared to unmodified ACTH. For example, ACTH analog compounds can include Ala residues substituted for the unmodified ACTH residues at one or more positions in formula (III). ACTH analog compounds can include residue substitution of SEQ ID NO: 5 in formula (III) of Gly, or any amino acid with an alkyl side chain (i.e., Ala, Val, Leu, Ile, or an amino acid analog comprising an alkyl side chain such as Nle). Also preferably, the ACTH analog can also include at least one Ala and at least one Arg residue substituted at any two of the amino acid positions 15, 16, 17 or 18 of SEQ ID NO:2. Optionally, the ACTH analog substitutions at positions 15, 16, 17, or 18 of SEQ ID NO:2 are amino acids selected from the group consisting of: Lys, Arg, Ala, Gly, Val, Leu, Ile, an amino acid analog comprising an alkyl side chain such as Nle, Gln, Asn, Glu, and Asp. Most preferably, the ACTH analogs comprise an amino acid sequence according to formula (III) selected from the group consisting of: Lys-Arg-Ala-Ala- (SEQ ID NO:6), Ala-Lys-Ala-Arg (SEQ ID NO:7), Lys-Ala-Ala-Arg (SEQ ID NO:8), Lys-Ala-Arg-Ala- (SEQ ID NO:9), Gln-Lys-Gln-Arg (SEQ ID NO:10) and Ala-Ala-Ala-Ala (SEQ ID NO:11). ACTH analog compounds can also include the substitution of one or more amino acid residues at positions 15, 16, 17 or 18 with an amino acid or amino acid analog having an alkyl side chain, including Gly, Ala, Val, Leu, Ile or Nle. ACTH analogs include other amino acids substituted at one or more of the $AA^{15}$-$AA^{16}$-$AA^{17}$-$AA^{18}$ positions that preserve one or more preferred biological functions of ACTH analog compounds, such as the reduction of corticosteroid secretion by the ACTH analog compared to unmodified ACTH, reduction of corticosteroid secretion by endogenous ACTH and/or MC-2R binding.

The $(AA^{19})$- portion of formula (I) represents an amino acid residue that is can be Pro, Trp or Ala, but is preferably Trp, Ala or other amino acids that can be substituted at the $(AA^{19})$- position while preserving one or more preferred biological functions of ACTH analog compounds, such as the reduction of corticosteroid secretion by the ACTH analog compared to unmodified ACTH, reduction of corticosteroid secretion by endogenous ACTH and/or MC-2R binding. Preferably, the ACTH analog compounds have an amino acid other than Proline substituted at the $(AA^{19})$- position. More preferably, the ACTH analogs include the amino acid Trp substituted at the $(AA^{19})$- position, instead of Pro. Unmodified ACTH peptide sequences, such as hACTH and mACTH, comprise a proline residue at the $(AA^{19})$- position. Proline has the following chemical structure:

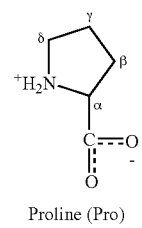

Proline (Pro)

The chemical structure of Proline includes a side-chain that forms a ring structure. Proline is often found at the end of a helix or in turns or loops. Unlike other amino acids which exist almost exclusively in the trans-form in polypeptides, proline can exist in the cis-configuration in peptides. The cis and trans forms are nearly isoenergetic. Preferably, $(AA^{19})$- is Trp in ACTH analogs comprising SEQ ID NOs:6-10 at formula (III), although compounds where $(AA^{19})$- is Pro in ACTH analogs are also provided.

Accordingly, particularly preferred ACTH analogs are modified hACTH, mACTH or hACTH(1-24) peptide sequences where $(AA^{14})$-$(AA^{15-18})$-$(AA^{19})$- are selected from the group consisting of: -Gly$^{14}$-Lys$^{15}$-Arg$^{16}$-Ala$^{17}$-Ala$^{18}$-Trp$^{19}$- (SEQ ID NO:12); -Gly$^{14}$-Ala$^{15}$-Lys$^{16}$-Ala$^{17}$-Arg$^{18}$-Pro$^{19}$- (SEQ ID NO:13); -Gly$^{14}$-Lys$^{15}$-Ala$^{16}$-Ala$^{17}$-Arg$^{18}$-Pro$^{19}$- (SEQ ID NO:14); -Gly$^{14}$-Lys$^{15}$-Ala$^{15}$-Arg$^{17}$-Ala$^{18}$-Pro$^{19}$- (SEQ ID NO:15); -Gly$^{14}$-Gln$^{15}$-Lys$^{16}$-Gln$^{17}$-Arg$^{18}$-Pro$^{19}$- (SEQ ID NO:16) and -Gly$^{14}$-Lys$^{15}$-Arg$^{16}$-Ala$^{17}$-Ala$^{18}$-Pro$^{19}$- (SEQ ID NO:17).

The ACTH analog is comprising a polypeptide described by formula (IVa) or formula (IVb):

$$N\text{-}(AA^{1-13})\text{-}(AA^{14})\text{-}(AA^{15-18})\text{-}(AA^{19})\text{-}(AA^{20-24})\text{-} \quad (IVa)$$

$$N\text{-}(AA^{1-13})\text{-}(AA^{14})\text{-}(AA^{15-18})\text{-}(AA^{19})\text{-}(AA^{20-24})\text{-Ac} \quad (IVb)$$

where N- indicates the N-terminal end of the polypeptide, Ac indicates the carboxy terminal end of the polypeptide. The ACTH analogs of formula (VIa) or (VIb) include the N- $(AA^{1-13})$-$(AA^{14})$-$(AA^{15-18})$-$(AA^{19})$- as described with respect to formula (I) above, and further comprise the $(AA^{20-24})$ portion attached to the carboxy end of the amino acid sequence of formula (I). The (AA$^{20-24}$)- portion of formula (VIa) and (VIb) represents a sequence of five amino acids of formula (V):

$$-AA^{20}-AA^{21}AA^{22}AA^{23}-AA^{24}-. \quad (V)$$

The (AA$^{20-24}$)- portion of unmodified human ACTH comprises the sequence Val-Lys-Val-Tyr-Pro (SEQ ID NO:18). Preferably, ACTH analog compounds include substitution of one or more amino acid residues in formula (V) extend the serum half life of the ACTH analog. For example, an ACTH analog can comprise a sequence corresponding to formula (V) of: -Ala-Ala-Ala-Ala-Ala- (SEQ ID NO:19).

Particularly preferred ACTH analog according to formula (IVa) comprise the sequence hACTH(1-24) with substitution of the -AA$^{15}$-AA$^{16}$-AA$^{17}$-AA$^{18}$- portion of formula (III) with SEQ ID NO:6. One particularly preferred compound of formula (IVa) is the ACTH analog (KKRRP15-19KRAAW) mACTH(1-24), having the sequence: N-Ser$^1$-Tyr-Ser-Met-Glu$^5$-His-Phe-Arg-Trp-Gly$^{10}$-Lys-Pro-Val-Gly-Lys$^{15}$-Arg-Ala-Ala-Trp-Val$^{20}$-Lys-Val-Tyr-Pro-Ac (SEQ ID NO:20), also referred to as "AT814". Other particularly preferred ACTH analog compounds consist essentially of the peptide of SEQ ID NO:2 with alanine or glutamine substitutions of one or more of the amino acid residues at positions 15, 16, 17 or 18, and/or substitution of the amino acid residues at positions 20, 21, 22, 23 or 24 with alanine, for example as described by Costa, J L et al., "Mutational analysis of evolutionarily conserved ACTH residues," Gen Comp Endocrinol. March; 136 (1):12-6 (2004), which is incorporated herein by reference in its entirety.

In a third aspect of the first embodiment, the ACTH analog is comprising a polypeptide described by formula (VIa) or formula (VIb):

$$N-(AA^{1-13})-(AA^{14})-(AA^{15-18})-(AA^{19})-(AA^{20-24})-(AA^{25-39})- \quad (VIa)$$

$$N-(AA^{1-13})-(AA^{14})-(AA^{15-18})-(AA^{19})-(AA^{20-24})-(AA^{25-39})-Ac \quad (VIb)$$

where N- indicates the amino-terminal end of the polypeptide, Ac indicates the carboxy-terminal end of the polypeptide. The ACTH analogs of formula (IVa) or (IVb) include the N-(AA$^{1-13}$)-(AA$^{14}$)-(AA$^{15-18}$)-(AA$^{19}$)-(AA$^{20-24}$)- as described above with respect to formula (IVa), and further comprise the (AA$^{25-39}$)- portion attached to the carboxy end of the amino acid sequence of formula (IVa). Formula (VIa) can optionally include additional chemical structures attached to the AA$^{39}$ residue, while the AA$^{39}$ residue forms the carboxy terminal end of the structures of formula (VIb). The (AA$^{25-39}$)- portion of formula (VIa) and (VIb) represents a sequence of fifteen amino acids of formula (VII):

$$-AA^{25}-AA^{26}AA^{27}-AA^{28}-AA^{29}-AA^{30}-AA^{31}AA^{32}-AA^{33}-AA^{34}-AA^{35}-AA^{36}-AA^{37}-AA^{38}-AA^{39}. \quad (VII)$$

The (AA$^{25-39}$)- portion of unmodified human ACTH comprises the sequence Asn-Gly-Ala-Glu-Asp-Glu-Ser-Ala-Glu-Ala-Phe-Pro-Leu-Glu-Phe (SEQ ID NO:21). Preferably, ACTH analog compounds include substitution of one or more amino acid residues in formula (VII), or truncation of one or more amino acid residues from the carboxy-terminal end of formula (VII); that provide ACTH analog compounds with desired sustained release properties. For example, an ACTH analog can comprise a sequence corresponding to formula (VII) having the unmodified ACTH sequence of SEQ ID NO:10, optionally modified by substitution of Lys at AA$^{30}$ and/or substitution of Arg at AA$^{36}$.

Substitutional variants are those in which at least one residue in the amino acid sequence has been removed and a different residue inserted in its place. Such substitutions may be made in accordance with the following Table 2 when it is desired to finely modulate the characteristics of the protein. Table 2 shows amino acids which may be substituted for an original amino acid in a protein and which are regarded in the art as conservative substitutions. ACTH analog compounds include compounds with one or more conservative substitutions that retain one or more of the following preferred ACTH analog biological functions: (1) reduction of corticosteroid secretion by adrenal membrane in the presence of the ACTH analog compared to unmodified ACTH, (2) reduction of corticosteroid secretion by adrenal membrane in the presence of endogenous ACTH and (3) increased MC-2R binding affinity with reduced activation of the MC-2R receptor compared to unmodified ACTH.

TABLE 2

| Original Residue | Conservative Substitutions |
|---|---|
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than in Table 2, i.e., selecting residues that differ more significantly in their effect on maintaining: (a) the structure of the polypeptide backbone in the area of the substitution, for example, as a sheet or helical conformation; (b) the charge or hydrophobicity of the molecule at the target site; or (c) the bulk of the side chain. The substitutions which in general are expected to produce the greatest changes in protein properties will be those in which: (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The preferred ACTH analog biological functions of ACTH analog compounds can be measured by any suitable method, but are preferably assessed by performing one or more of the assays described below ACTH Analog Compounds with Decreased ACTH Function In a second embodiment, ACTH analogs are modified ACTH peptides that function to reduce corticosteroid secretion by adrenal membrane in the presence of the ACTH analog compared to unmodified ACTH. The structure of the ACTH analogs is preferably selected according to one or more of the structural formulae provided above. The ACTH analog compounds can have a reduced ACTH-mediated secretion of blood corticosterone, for example as measured by a reduction in the level of corticosteroid in the blood of a subject after administering the ACTH analog. ACTH analogs preferably demonstrate at least a 10%, 15%, 20%, 30%, 40%, 50%, 60%, 70%, 80%, 85%, 90%, 91%, 92%, 93%, 94%, 95%, 96%, 97%, 98%, 99% or 100% reduction in the serum corticosterone levels compared to the comparable administration of unmodified ACTH peptide, as measured by an in vivo Serum Corticosteroid Induction Assay.

An in vivo Serum Corticosteroid Induction Assay measures the level of corticosteroid or corticosterone in the blood stream of a subject. More specifically, the in vivo Serum Corticosteroid Induction Assay can include the following steps: first, an agent to suppress endogenous ACTH production was administered to a mouse subject, such as an intraperitoneal injection of dexamethasone; second, after waiting a suitable period of time for suppression of endogenous ACTH production (e.g., 1.5-2.0 hours), a test compound can be administered to the mouse by a suitable method, such as intraperitoneal or subcutaneous injection; and third, after waiting a suitable period of time (e.g., 1 hour) for action of the injected test compound, a blood sample can be taken from the subject and the level of serum corticosterone can be determined by a suitable method, such as a competitive radioimmunoassay using $^{125}$I RIA kit (ICN, Costa Mesa, Calif.). Example 1 describes a murine in vivo Serum Corticosteroid Induction Assay in detail.

The corticosteroid or corticosterone secretion induced in vivo by an ACTH analog compound was compared to the level of corticosteroid secretion produced by an unmodified ACTH compound by measuring blood serum corticosteroid after administering either the ACTH or ACTH analog as test compounds. FIG. 1 shows the results of murine in vivo Corticosteroid Adrenal Induction Assays performed with mACTH(1-24) and various ACTH analog test compounds according to the method of Example 1. ACTH analog compositions with decreased function were identified by measuring corticosterone levels using standard radioimmunoassay (RIA) analysis on blood samples collected one hour after administering the mACTH(1-24) or ACTH analog compound to dexamethasone-suppressed mice. In FIG. 1, the potency of various ACTH analog peptides is expressed as percent induction of corticosterone, with mouse ACTH being 100%. The graph 10 shows the percent corticosterone induction 12 for ACTH and nine samples 14 of ACTH analog Compounds. The percent of corticosterone induction 12 of ACTH analog Compounds in Samples 2-10 are shown as a percentage of the concentration of serum corticosterone 20 measured for unmodified mACTH(1-24) in the in vivo Serum Corticosteroid Adrenal Induction Assay. The structural modifications and measured percentage reduction in serum measured for Samples 2-10 in FIG. 1 are shown in Table 3 below.

TABLE 3

| Sample | Label in FIG. 1 | Structural Modification | Percent reduction in serum corticosteroid |
|---|---|---|---|
| 2 | 20 | (V26F, E30K)mACTH | 18.3% |
| 3 | 25 | (P19W, K21E, Y23R)mACTH | 36.5% |
| 4 | 30 | (E30K, P36R)mACTH | 41.5% |
| 5 | 35 | (PVKVYP19-24AAAAA)mACTH | 51% |
| 6 | 40 | (V26F, P36R)mACTH | 59.3% |
| 7 | 45 | (P19W, K21E)mACTH | 61.1% |
| 8 | 50 | (P19W, K21A, delY23)mACTH | 76.0% |
| 9 | 55 | (P19W, K21A)mACTH | 83.4% |
| 10 | 60 | (KKRRP15-19KRAAW)mACTH | 100% |

Reduction of Endogenous ACTH-Induced Corticosterone Induction

In a third embodiment, ACTH analogs are modified ACTH peptides that function to reduce corticosteroid secretion by adrenal membrane in the presence of endogenous ACTH. When administered before or concurrently with ACTH, ACTH analog compounds can produce a 10-100% reduction in serum corticosteroid levels. Preferably, ACTH analog compounds provide a reduction in the serum corticosteroid levels measured by an in vivo Serum Corticosteroid Inhibition Assay of about 10%, 15%, 20%, 30%, 40%, 50%, 60%, 70%, 80%, 85%, 90%, 91%, 92%, 93%, 94%, 95%, 96%, 97%, 98%, 99% or 100% compared to administration of ACTH alone, as measured by an in vivo Serum Corticosteroid Inhibition Assay, such as the assay described in Example 2. Exemplary ACTH analog compounds that inhibit adrenal hormone production induced by endogenous ACTH were identified by performing a series of in vivo Serum Corticosteroid Inhibition Assays. ACTH analogs can be administered alone, prior to ACTH administration, or concurrently in combination with ACTH.

An in vivo Serum Corticosteroid Inhibition Assay measures the level of corticosteroid or corticosterone in the blood stream of a subject after administering a compound having a first corticosteroid-producing biological activity and a test compound. The compound having the corticosteroid-producing biological activity can be any compound known to induce a detectable increase in corticosteroid production. The test compound can be administered before the corticosteroid-producing compound, in combination with the corticosteroid-producing compound, and/or after the corticosteroid-producing compound. The corticosteroid-producing compound is preferably ACTH, but can also be an ACTH analog with a known corticosteroid-producing biological activity. By performing a series of in vivo Serum Corticosteroid Inhibition Assays using ACTH analog test compounds, ACTH analogs that inhibit the production of corticosteroid relative to the corticosteroid-producing compound used can be identified. Preferably, the ACTH analogs identified in this manner inhibit the production of corticosteroid in the presence of endogenous unmodified ACTH.

The in vivo Serum Corticosteroid Inhibition Assay can include sequential administration of the test compound and the corticosteroid-producing compound by the following steps: first, an agent to suppress endogenous ACTH production was administered to a mouse subject, such as an intraperitoneal injection of dexamethasone; second, after waiting a suitable period of time for suppression of endogenous ACTH production (e.g., 1.5-2.0 hours), a test compound was administered to the mouse by a suitable method, such as intraperitoneal injection; third, after waiting a suitable period of time (e.g., 1 hour) for action of the test compound, a compound with corticosteroid-producing activity can be administered to the mouse by a suitable method, such as intraperitoneal injection; and fourth, after waiting a suitable period of time for the biological activity of both administered compounds to occur (e.g., 1 hour), a blood sample was taken from the subject and the level of serum corticosterone was determined by a suitable method, such as a competitive radioimmunoassay using $^{125}$I RIA kit (ICN, Costa Mesa, Calif.). Optionally, steps two and three can be reversed (administering the corticosteroid-producing compound first, followed by administration of the test compound). The in vivo Serum Corticosteroid Inhibition Assay can also include co-administration of the test compound and the corticosteroid-producing compound by the following steps: first, an agent to suppress endogenous ACTH production was administered to a mouse subject, such as an intraperitoneal injection of dexamethasone; second, after waiting a suitable period of time for suppression of endogenous ACTH production (e.g., 1.5-2.0 hours), the corticosteroid-producing compound and a test compound were co-administered to the mouse by a suitable method, such as intraperitoneal injection; and third, after waiting a suitable period of time for the biological activity of both administered compounds to occur (e.g., 1 hour), a blood sample was taken from the subject and the level of serum corticosterone was determined by a suitable method, such as a competitive radio-immunoassay using $^{125}$I RIA kit (ICN, Costa Mesa, Calif.). Also, in some embodiments, the first step in any in vivo Serum Corticosteroid Inhibition Assay can be replaced by a measurement of the initial endogenous corticosteroid or corticosteroid level in the blood of the subject in the manner of step four, instead of administering the agent to suppress ACTH production. Example 2 describes murine in vivo Serum Corticosteroid Inhibition Assays in detail.

A series of separate in vivo Serum Corticosteroid Inhibition Assays were performed to identify ACTH analogs that inhibit ACTH adrenal hormone production in vivo. The serum corticosterone levels of dexamethasone-suppressed mice were measured as described in Example 2 after administration of (1) ACTH (corticosteroid-producing compound), (2) an ACTH analog (test compound) followed by subsequent administration of ACTH, (3) a combination of ACTH and the ACTH analog and (4) the ACTH analog alone. Table 4 shows the level of serum corticosteroid measured in the mice as a function of time of administration.

TABLE 4

Combined administration of ACTH and an ACTH analog

| | Time | | | |
|---|---|---|---|---|
| Sample | 0 minutes | 90 minutes | 120 minutes | 180 minutes |
| Vehicle | Dexamethasone (administered to all groups) | | Vehicle | 0 ± 0 ng/mL |
| ACTH | | | mACTH(1-24) | 500 ± 76 ng/mL |
| AT90-ACTH120 | | (KKRRP15-19KRAWW) mACTH(1-24) | mACTH(1-24) | 175 ± 27 ng/mL |
| (AT + ACTH)120 | | | (KKRRP15-19KRAAW) mACTH(1-24) + mACTH(1-24) | 51 ± 8 ng/mL |
| AT | | | (KKRRP15-19KRAAW) mACTH(1-24) | 7 ± 7 ng/mL |

Referring to Table 4, dexamethasone was first administered at time=0 minutes to mice in five separate in vivo Serum Corticosteroid Assays, as described in Example 2. In the "Vehicle" sample, the liquid vehicle alone was administered 120 minutes after dexamethasone injection, resulting in an undetectable level of corticosterone measured in a blood sample taken one hour later. In the "ACTH" sample, ACTH was administered 120 minutes after dexamethasone injection, resulting in a level of 500±76 ng/mL of corticosterone detected in a blood sample taken one hour later. In the "AT90-ACTH 120" sample, the ACTH analog (KKRRP15-19KRAAW) mACTH(1-24) was administered at 1.5 hours after dexamethasone injection, ACTH(1-24) was administered 30 minutes later, and a serum corticosterone level of 175±27 ng/mL was measured in a blood level taken one hour later. In the "(AT+ACTH)120" sample, the ACTH analog (KKRRP15-19KRAAW) mACTH(1-24) ("AT814") was administered together with mACTH(1-24) 120 minutes after dexamethasone injection, and a serum corticosterone level of 51±8 ng/mL was measured in a blood level taken one hour later. In the "AT" sample, the administration of the ACTH analog (KKRRP15-19KRAAW) mACTH(1-24) 120 minutes after dexamethasone injection resulted in a negligible level of serum corticosterone level of about 7±7 ng/mL.

FIG. 2 shows the results from Table 2 as a percentage of the level of corticosterone levels measured at 180 minutes after dexamethasone injection, as described in Example 2. The graph 100 shows the percent corticosterone induction 112 for ACTH and four samples 114 described in Table 2, with the level of corticosterone measured for administration of the ACTH 120 being normalized to 100%. Sample "AT90-ACTH 120" 140 shows the administration of the ACTH analog 30 minutes before administration of the ACTH, which resulted in about a 65% reduction in serum corticosterone levels in blood samples taken one hour after ACTH administration. Sample "(AT+ACTH)120" 160 shows the concurrent administration of the ACTH analog with the ACTH and resulted in about a 90% reduction in serum corticosterone levels in blood samples taken one hour later. As seen in the "AT" Sample 180, as well as Sample 10 of Table 1, the administration of the ACTH analog alone again resulted in about a 99%-100% reduction in serum corticosterone levels in blood samples taken one hour later. The "Vehicle" only sample is not shown in FIG. 2.

Adrenal ACTH Receptor Binding Assay

In a fourth embodiment, ACTH analogs are modified ACTH peptides that function to bind to adrenal ACTH receptors, such as the MC-2R receptor, preferably with increased MC-2R binding affinity and reduced activation of the MC-2R receptor compared to unmodified ACTH.

Preferred ACTH analog compounds bind to adrenal membranes with a greater affinity than endogenous unmodified ACTH, and are able to displace unmodified ACTH in an in vitro Serum-free Adrenal Competitive Binding Assay (Example 3). ACTH analog compounds preferably displace at least 20% of ACTH binding to adrenal membrane preparations as measured by the in vitro Serum-free Adrenal Competitive Binding Assay. More preferably, ACTH analog compounds can have a 2-, 3-, 4-, 5-, 10-, 20-, 30-, 40-, 50-, 60-, 70-, 80-, 90-, 100-fold greater affinity for explanted adrenal membrane compared to unmodified ACTH.

ACTH analog compounds that bind to adrenal membrane with a greater affinity than endogenous unmodified ACTH, and are able to displace unmodified ACTH can be identified using an in vitro Serum-free Adrenal Competitive Binding Assay (Example 3). FIG. 3 shows the results of an in vitro Serum-free Adrenal Competitive Binding Assay performed by the method described in Example 3 using the exemplary ACTH analog AT814, having SEQ ID NO:20 ("AT814"). The graph 200 shows the counts per minute 212 (CPM) measured by a gamma counter in adrenal membrane preparations incubated with radioactive ACTH. A higher CPM level indicates the presence of greater amounts of the radiolabelled compound. Column 210 shows the background measurement without any adrenal membrane present. Column 220 indicates the level of radio-labeled unmodified mACTH(1-24) detected after combining the explanted adrenal membrane with only the radio-labeled mACTH(1-24) for 2 hours (no competitive binding). Columns 230, 240, and 250 show the results of competitive binding assays for binding of non-radio-labeled ("cold") mACTH(1-24) to displace the radio-labeled mACTH(1-24) from the explanted adrenal membrane (measured in column 220) by competitive binding to receptors such as MC-2R on the adrenal membrane. Specifically, column 230 indicates a decrease in the level of radio-labeled mACTH(1-24) detected after combining the radio-labeled explanted adrenal membrane with 10 nM "cold" mACTH(1-24); column 240 indicates additional reduction in the level of radio-labelled mACTH(1-24) bound to the radio-labeled explanted adrenal membrane after adding 100 nM "cold" mACTH(1-24); and Column 250 indicates further reduction in the level of radio-labelled mACTH(1-24) attached to the radio-labeled explanted adrenal membrane after combining an explanted adrenal membrane preparation with 1000 nM of "cold" mACTH(1-24). The decreasing levels of radio-labeled mACTH(1-24) detected as the concentration of "cold" mACTH(1-24) is increased indicates a displacement of the radio-labeled mACTH(1-24) by the "cold" mACTH(1-24) from the MC-2R receptor.

The in vitro Serum-free Adrenal Competitive Binding Assay was repeated using the "cold" (non-radio-labeled) AT814 ACTH analog compound described by SEQ ID NO:20, instead of the mACTH(1-24). Columns 235, 245, and 255 show the results of competitive binding assays for binding of non-radio-labeled AT814 to displace the radio-labeled mACTH(1-24) from the explanted adrenal membrane (measured in column 220) by competitive binding of "cold" AT814 at concentrations of 10 nM (column 235), 100 nM (column 245) and 1000 nM (column 255). The decreasing levels of radio-labeled AT814 detected as the concentration of "cold" AT814 is increased indicates a displacement of the radio-labeled mACTH(1-24) by the "cold" AT814. Specifically, the results in graph 200 indicate that AT814 has an increased affinity to bind to the adrenal membrane that is about 3- to about 4-fold greater than the radio-labeled mACTH(1-24). The increased affinity of AT814 binding to adrenal membrane can be indicative of increased MC-2R receptor binding affinity.

Testing of ACTH analog Compounds In Vitro

In a fifth embodiment, ACTH analog compounds can reduce corticosterone induction by unmodified ACTH in explanted tissue in vitro. When combined with explanted adrenal membrane ACTH analog compounds preferably produce a 10-100% reduction in corticosteroid levels in serum-free media. Preferably, ACTH analog compounds provide a reduction in the serum corticosteroid levels measured by an in vitro Serum-Free Adrenal Corticosteroid Inhibition Assay of about 10%, 15%, 20%, 30%, 40%, 50%, 60%, 70%, 80%, 85%, 90%, 91%, 92%, 93%, 94%, 95%, 96%, 97%, 98%, 99% or 100% compared to administration of unmodified ACTH alone (Example 4). Exemplary ACTH analog compounds that inhibit adrenal hormone production induced by exposing explanted adrenal membrane to unmodified ACTH were identified by performing a series of in vitro Serum-Free Adrenal Corticosterone Inhibition Assays, suggesting a direct action of ACTH analog compounds on adrenal corticosterone production.

A series of separate in vitro Serum-Free Adrenal Corticosteroid Inhibition Assay were performed to identify ACTH analogs that inhibit ACTH-induced adrenal hormone production in vitro. The concentration of corticosterone was measured according to the procedure of Example 4 in a serum-free culture medium containing explanted adrenal membrane and unmodified ACTH, AT814 ACTH analog (SEQ ID NO:20), or a combination of ACTH and AT814 at 100 ng/mL each. Table 3 shows the level of corticosteroid measured in the serum free medium in a series of in vitro Serum-Free Adrenal Corticosterone Inhibition Assays performed using explanted mouse adrenal membrane. Corticosterone levels were taken at 2.0 hours after the adrenal membrane was placed in the serum free M199 medium, and each corticosterone level in Table 5 is an average of five samples.

TABLE 5

Combined administration of ACTH and an ACTH analog

| Sample | 0 hrs. | 0.5 hrs. | 2.5 hrs. |
| --- | --- | --- | --- |
| M199 Medium | Incubate tissue in M199 serum-free medium (applied to all samples) | | 278 mg/ml |
| ACTH | | ACTH | 600 mg/ml |
| AT-814 | | AT814 | 290 mg/ml |
| ACTH + AT814 | | ACTH + AT814 | 396 mg/ml |

Referring to Table 5, explanted mouse adrenal halves were placed in an M199 serum free medium (Invitrogen) for 30 minutes, as provided in Example 4. In the "M199 Medium" samples, the adrenal membrane was soaked in the M199 serum-free medium for a total of 2.0 hours after the initial 30 minutes (2.5 hours total), before the corticosterone level in the culture was measured using standard RIA radioassay techniques. In the "ACTH" samples, unmodified ACTH was added to the M199 medium, resulting in a level of about 600 mg/mL of corticosterone detected in the culture medium two hours later. In the "AT-814" sample, the ACTH analog (KKRRP15-19KRAAW) mACTH(1-24) (SEQ ID NO:20) was added to the M199 medium, resulting in a level of about 290 mg/mL of corticosterone detected in the culture medium two hours later. In the "ACTH+AT-814" sample, 100 ng/mL of AT814 ACTH analog (SEQ ID NO:20) and 100 ng/mL of unmodified ACTH was added together to the M199 medium, resulting in a level of about 396 mg/mL of corticosterone detected in the culture medium two hours later. FIG. 4 is a graph 300 showing the percent corticosterone induction 302 from Table 3 as a percentage relative to the amount of ACTH 310 measured in the M199 culture medium for the "ACTH" sample 310, the "AT-814" sample 320 and the "ACTH+AT-814" sample 330, as described above and in Example 4. The "M199 Medium" sample is not shown in FIG. 2. Referring again to FIG. 4, the addition of the AT814 to the adrenal membrane in the M199 serum-free medium permitted only a negligible amount of corticosterone induction, and addition of the combination of equal amounts of the AT814 ACTH analog and unmodified ACTH reduced the amount of corticosterone induction by about 65% compared to addition of the unmodified ACTH alone.

Testing of ACTH Analog Compounds In Vivo

ACTH analog compounds with extended serum half lives can be preferred for certain applications. ACTH analog compounds can optionally include one or more amino acid substitutions or truncations that can extend the serum half life of the ACTH analog relative to unmodified ACTH or another ACTH analog. For example, ACTH analog compounds can comprise one or more amino acid substitutions from the amino acid positions 25-39 of an unmodified ACTH sequence that that extend the serum half life of the compound relative to the ACTH sequence. Preferred ACTH analog compounds can have a serum half life that is greater than that of unmodified ACTH. The half life of ACTH in blood is less than about 20 minutes. Therefore, particularly preferred ACTH analog compounds have a serum half life of about 20, 30, 40, or 50 minutes or greater.

In a sixth embodiment, extended half-life ACTH analogs are provided. Extended half-life ACTH analogs can be identified as having a first activity measured by the concentration of serum corticosteroid detected in vivo that is greater than a second activity measured by the serum-free concentration of corticosteroid detected in the in vitro activity, where the in vivo activity is measured by the Serum Adrenal Corticosteroid Inhibition Assay of Example 1 and the in vitro activity is measured by in vitro Serum-Free Adrenal Corticosteroid Inhibition Assay of Example 4.

While amino acid substitutions at other positions may also enhance ACTH analog serum half life in some circumstances, certain embodiments provide for extending the serum half life of an ACTH analog by modifying one or more amino acids at the 20-24 positions of an ACTH molecule, including hACTH or mACTH. FIG. 5 is a graph comparing the in vivo activity (grey bars) and in vitro activity (white bars) of seven ACTH analog compounds, 410, 420, 430, 440, 450, 460, and 470. For all seven ACTH analog compounds, the in vivo activity was measured using the method of Example 1 and the in vitro activity was measured using the method of Example 4. The results are provided as a bar graph of the "% corticosterone induction" 402 measured as a percentage relative to the mACTH(1-24) sequence (SEQ ID NO:2). As seen in FIG. 5, sample 460, designated "Ala19-24" refers to the ACTH analog (AAAAA20-24VKVYP)ACTH(1-24), comprising a substitution of Ala residues at each of the amino acid 19-24 positions of mACTH. Sample 460 showed an increased serum half life measured in vivo 462 relative to both the in vitro activity 464 measured for this compound, as well as being about 50% greater than the in vitro activity of unmodified mACTH. Furthermore, the in vivo activity of the (AAAAA20-24VKVYP)ACTH(1-24) ACTH analog 460 was greater relative to both mACTH and to other ACTH analogs 410, 420, 430, 440, 450 and 470. These results suggest that the amino acid residues at the 20-24 positions may play a role in determining the serum half life of an ACTH analog compound. ACTH analog compounds with one or more amino acid substitutions at the 20-24 positions of ACTH are particularly preferred for extending the serum half life relative to ACTH.

Also desirably, ACTH analog compounds can include amino acid substitutions that extend the serum half life without appreciably increasing, or more preferably decreasing, the corticosterone induction of the ACTH analog, as measured by in vivo (Example 1) or in vitro (Example 4) Assays. For example, corticosterone induction from substitutions of the 15-19 positions in ACTH analogs 410, 420, 430, 440, 450 and 470 reduced both the in vivo and in vitro corticosterone induction activity of the ACTH analogs compared to unmodified mACTH(1-24). Specifically, ACTH analog 410 is a (K15A, R17A)mACTH(1-24) ACTH analog that demonstrated an in vitro activity 414 that was greater than its in vivo activity 412; ACTH analog 420 is a (K16A, R17A)mACTH (1-24) ACTH analog that demonstrated an in vitro activity 424 that was greater than its in vivo activity 422; ACTH analog 430 is a (K16A, R18A)mACTH(1-24) ACTH analog that demonstrated an in vitro activity 434 that was greater than its in vivo activity 432; ACTH analog 440 is a (K15Q, R17Q)mACTH(1-24) ACTH analog that demonstrated an in vitro activity 444 that was greater than its in vivo activity 442 and ACTH analog 470 is a (P19W, K21A)mACTH(1-24) ACTH analog that demonstrated an in vitro activity 474 that was greater than its in vivo activity.

Screening Methods

In a seventh embodiment, methods for screening ACTH analogs that are useful in blocking excess ACTH while maintaining adrenal tone are also provided. Various ACTH analogs can be prepared and administered to a patient to assess in vivo cortisone induction.

The specificity of molecular recognition of certain compounds (i.e., antigens by antibodies) to form a stable complex can serve as the basis of both the analytical immunoassay in solution and the immunosensor on solid-state interfaces. These analytical methods can be ligand-binding assays based on the observation of the products of the ligand-binding reaction between the target analyte (i.e., a compound that binds to MC2R receptors) and a highly specific binding reagent.

In certain instances, alternative analyte-binding compounds such as aptamers are applied to ligand-binding assays for particularly sensitive screening. Aptamers are single-stranded DNA or RNA oligonucleotide sequences with the capacity to recognize various target molecules with high affinity and specificity. These ligand-binding oligonucleotides mimic properties of antibodies in a variety of diagnostic formats. They are folded into unique overall shapes to form intricate binding furrows for the target structure. Aptamers are identified by an in vitro selection process known as systematic evolution of ligands by exponential enrichment (SELEX). Aptamers may have advantages over antibodies in the ease of depositing them on sensing surfaces. Moreover, due to the highly reproducible synthetic approach in any quantities, albeit the affinity constants are consistently lower than those of antibodies and the stability of these compounds is still questionable, they may be particularly useful for screening applications in complex biological matrices (i.e., in identifying ACTH analogs with substituted amino acid residues at ACTH-(15-19) and/or ACTH-(21) positions that are particularly active in binding the MC2R).

Alternatively, molecular imprinting techniques may be used to screen compounds or methods that affect MC2R activity. This is a technique that is based on the preparation of polymeric sorbents that are selectively predetermined for a particular substance, or group of structural analogs. Functional and cross-linking monomers of plastic materials, such as methacrylics and styrenes, are allowed to interact with a templating ligand to create low-energy interactions. Subsequently, polymerization is induced. During this process, the molecule of interest is entrapped within the polymer either by a noncovalent, self-assembling approach, or by a reversible, covalent approach. After stopping the polymerization, the template molecule is washed out. The resultant imprint of the template is maintained in the rigid polymer and possesses a steric (size, shape) and chemical (special arrangement of complementary functionality) memory for the template. The molecularly imprinted polymer (MIP) can bind the template (=analyte) with a specificity similar to that of the antigen-antibody interaction.

Besides the main applications in solid-phase extraction and chromatography, molecularly imprinted polymers can be employed as nonbiological alternatives to antibodies in competitive binding assays. During the growth of a typical biological cell, carbon-containing nutrients such as glucose are taken up and acidic metabolic products such as lactic acid are released. In microphysiometry, these changes in metabolic rate are recorded as changes in the rate of acidification of the medium surrounding the cells (i.e., Raley-Susman, K. M. et al., "Effects of excitotoxin exposure on metabolic rate of primary hippocampal cultures: application of silicon microphysiometry to neurobiology," *J Neurosci.*, 12(3):773-780 (1992); Baxter, G. T. et al., "PKCε is involved in granulocyte-macrophage colony-stimulating factor signal transduction: evidence from microphysiometry and antisense oligonucleotide experiments," *Biochemistry*, 31:19050-10954 (1992); Bouvier, C. et al., "Dopaminergic activity measured in $D_1$- and $D_2$-transfected fibroblasts by silicon microphysiometry," *J. Recept. Res.*, 13(1-4):559-571 (1993); and McConnell, H. M. et al., "The cytosensor microphysiometer: biological applications of silicon technology," *Science*, 257:1906-1912 (1992)). Microphysiometry can be used to detect molecules that affect the cell. Such molecules include neurotransmitters, growth factors, cytokins, receptors, and the like. Thus, the microphysiometry method can provide valuable information regarding ACTH analogs that affect MC2R receptor activity.

Synthetic combinatorial libraries can be a source of diverse structures useful for large-scale biochemical screening (i.e., Sastry, L. et al., "Screening combinatorial antibody libraries for catalytic acyl transfer reactions," *Ciba Found Symp.*, 159: 145-155 (1991); Persson, M. A. A. et al., "Generation of diverse high-affinity monoclonal antibodies by repertoire cloning," *Proc. Natl. Acad. Sci. USA*, 33:2432-2436 (1991); and Houghten, R. A., "Generation and use of synthetic peptide combinatorial libraries for basic research and drug discovery," *Nature*, 354:84-86 (1991)). Such libraries are generated by a combination of solution and solid-phase chemistries and are cleaved off the solid-support for screening.

Separation techniques such as liquid chromatography, gas chromatography, and capillary electrophoresis coupled to mass spectrometry or tandem-mass spectrometry create analytical systems available for structural evaluation (i.e., Hsieh, S. et al., "Separation and identification of peptides in single neurons by microcolumn liquid chromatography—Matrix-assisted laser desorption/ionization time-of-flight mass spectrometry and postsource decay analysis," *Anal Chem.*, 70(9): 1847-1852 (1998); Tretyakova, N. Y. et al., "Quantitative analysis of 1,3-butadiene-induced DNA adducts in vivo and in vitro using liquid chromatography electrospray ionization tandem mass spectrometry," *J. Mass Spectrom.*, 33:363-376 (1998); and Taylor, G. W. et al., "Excursions in biomedical mass spectrometry," *Br. J. Clin. Pharmacol.*, 41:119-126 (1996)). Mass spectrometry is particularly useful in providing information about the molecular weight of a compound/molecule. With refined and controlled fragmentation of large molecules, it is also possible to extract information about the sequence.

Methods of screening ACTH analog compounds to identify ACTH analog compounds that induce less corticosteroid secretion by adrenal membrane than unmodified ACTH of SEQ ID NO:2 or SEQ ID NO:1 can include the step of contacting an adrenal membrane with an ACTH analog. Methods of screening ACTH analog compounds to identify compounds with reduced ACTH-induced secretion of corticosteroid can include one or more of the following steps:
 a. providing a first adrenal membrane and a second adrenal membrane;
 b. contacting the first adrenal membrane a first composition comprising an unmodified peptide comprising an unmodified ACTH peptide, and subsequently measuring a first concentration of corticosteroid secreted by the first adrenal membrane after contact with the unmodified ACTH peptide;
 c. contacting the second adrenal membrane with a second composition comprising the ACTH analog, and subsequently measuring a second concentration of corticosteroid secreted by the second adrenal membrane after contacting the ACTH analog;
 d. comparing the first concentration of corticosteroid secreted with the second concentration of corticosteroid secreted; and
 e. determining whether the second compound induces less corticosteroid secretion than the first compound.

The unmodified ACTH peptide is preferably the peptide of SEQ ID NO:2 or SEQ ID NO:1.

The first adrenal membrane and the second adrenal membrane can be positioned within a subject and the concentration of corticosteroid can be measured in the blood of the subject (in vivo assays). Alternatively, the first adrenal membrane and the second adrenal membrane are explanted from the subject and wherein the concentration of corticosteroid is measured in serum-free media (in vitro assays). Screening Assays comprising in vivo Inhibition Assay steps or in vitro competitive binding assay steps, can also include the following step, which is preferably performed either in place of or after step (c) and before step (d):
 a. simultaneously contacting the second adrenal membrane with the first composition comprising the ACTH peptide and the second composition comprising the ACTH analog, and subsequently measuring a second concentration of corticosteroid secreted by the second adrenal membrane.

Screening assays can include steps of performing one or more other assays, including the assays described as the Serum Corticosteroid Induction Assay, Serum Corticosteroid Inhibition Assay, Adrenal Binding Assay, or Serum-Free Adrenal Inhibition Assay. Steps can be performed in any order, unless otherwise specified.

ACTH Analog Compositions and Administration

The ACTH analogs can be incorporated in pharmaceutical compositions for treating various ACTH-related conditions, including conditions related to the over-expression of ACTH in patients.

The phrase "pharmaceutically acceptable" or "pharmacologically acceptable" refer synonymously to ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "therapeutically effective amount" of a compound such as an ACTH analog peptide, with respect to use in treatment, refers to an amount of the polypeptide or peptide in a preparation which, when administered as part of a desired dosage regimen (to a chordate, such as a mammal or fish) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "treat" or any derivative thereof (i.e., treatment, treating), as used herein, refers to and includes: 1) preventing a disease or condition associated with high levels of ACTH from occurring in a patient that may be predisposed to such disease or condition but has not yet been diagnosed as having it; 2) inhibiting the disease or condition associated with high levels of ACTH, e.g., arresting its development; or 3) relieving the disease or condition associated with high levels of ACTH, e.g., causing regression of the disease or condition.

A "patient," or "subject," are used synonymously herein to refer to an organism, preferably a chordate animal such as a mammal, fish or avian species, for which treatment is provided in accordance with the present invention. Mammalian species that benefit from the disclosed ACTH analogs and methods of treatment include, but are not limited to, apes, chimpanzees, orangutans, humans, monkeys; and domesticated animals (e.g., pets) such as dogs, cats, mice, rats, guinea pigs, and hamsters. Fish species include salmon and other species used in aquaculture.

The term "ACTH-related condition" is used herein to refer to conditions, disorders, symptoms or diseases that may be treated by, or are responsive to, the regulation of ACTH-mediated corticosteroid or corticosteroid levels, regulation of ACTH-binding to adrenal membrane, or regulation of an ACTH-receptor such as MC-2R including certain melanocortin-receptor associated conditions.

The term "melanocortin-receptor associated condition" is used herein to refer to conditions, disorders, or diseases that may be treated by regulation of a receptor that binds ACTH, and/or by reduction in corticosteroid levels in a subject. An ACTH-related condition can include "MC-2R associated conditions," or conditions, disorders or diseases that may be treated by regulation of the MC-2R receptor. Preferably, MC-2R associated conditions can be treated by binding the MC-2R receptor with an ACTH analog that results in a reduced level of corticosteroid secretion compared to the level of corticosteroid secretion by endogenous ACTH.

All stereoisomers of the compounds identified using methods of the invention, including enantiomeric and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the compounds identified by the present invention can have the S or R, or D or L, configuration as defined by the IUPAC 1974 Recommendations.

In an eighth embodiment, the present disclosure pertains to pharmaceutical compositions comprising ACTH analogs, and the administration thereof to a subject in a manner commensurate with treatment for symptoms associated with an ACTH-related condition. The route of administration can be selected in accord with known methods. ACTH analogs can be employed as part of a pharmaceutical composition including a pharmaceutically-acceptable carrier. The pharmaceutical compositions comprising at least one ACTH analog of the invention to treat a disease or condition associated with elevated levels of ACTH, may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

Pharmaceutical compositions comprising ACTH analogs can be administered by any suitable means. For example, compositions comprising ACTH analogs can be administered by injection by subcutaneous, intravenous, intramuscular, or intracisternal injection or infusion techniques (e.g., as sterile injectable aqueous or non-aqueous solutions or suspensions); nasally, such as by inhalation spray; or topically, such as in the form of a cream or ointment; and in dosage unit formulations containing non-toxic, pharmaceutically-acceptable vehicles or diluents. ACTH analogs of the invention may, for example, be administered in a form suitable for immediate release or extended release. Immediate release or extended release may be achieved by the use of suitable pharmaceutical compositions comprising the ACTH analogs of the invention, or, particularly in the case of extended release, by the use of devices such as subcutaneous implants or osmotic pumps. The ACTH analogs of the invention may also be administered in the form of liposomes.

Pharmaceutical compositions comprising the ACTH analog polypeptides of the present invention can be formulated according to known methods, whereby the ACTH analog product hereof is combined in admixture with a pharmaceutically acceptable carrier vehicle. Compositions which may be used for the prophylactic and therapeutic treatment include one or more ACTH analog compounds and a means of application (such as an injectable carrier system, intranasal or transdermal mode).

"Carriers" as used herein include pharmaceutically acceptable carriers, excipients, or stabilizers which are nontoxic to the cell or subject being exposed thereto at the dosages and concentrations employed. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered kagacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient. Often, the physiologically acceptable carrier is an aqueous pH buffered solution. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids or amino acid derivatives such as norleucine or ornithene; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG. Any of the carriers for the ACTH analog may be manufactured by conventional means. However, if alcohol is used in the carrier, the ACTH analog should be in a micelle, liposome, or a "reverse" liposome, to prevent denaturing of the ACTH analog. Similarly, when the ACTH analog is being placed in the carrier, and the carrier is, or has been heated, such placement should be made after the carrier has cooled somewhat, to avoid heat denaturation of the ACTH analog. The carrier preferably is sterile. One or more ACTH analogs may be added to these substances in a liquid form or in a lyophilized state, whereupon it will be solubilized when it meets a liquid body.

Prior to, or at the time the modified ACTH analog can be combined with a carrier system, the ACTH analog may be in a stabilizing buffer environment for maintaining a pharmacologically suitable pH range, such as between about 4.0 and about 9.0, including a pH of about 5.0, 6.0, 7.0, 8.0 or any pH interval of 0.05 there between, or any interval that is a multiple of 0.05 there between, including pH values of 5.2, 6.5, 7.4, 7.5 and 8.5. Therapeutic formulations are prepared for storage by mixing the ACTH analog active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. A stabilizing buffer should allow for the optimum activity of the ACTH analog. The buffer may contain a reducing reagent, such as dithiothreitol. The stabilizing buffer also may be or include a metal chelating reagent, such as ethylenediaminetetracetic acid disodium salt, or it also may contain a phosphate or citrate phosphate buffer, or any other buffer.

The effective amount of a compound employed in the present invention may be determined by one of ordinary skill in the art. The effective dosage rates or amounts of the ACTH analog(s) will depend in part on whether the ACTH analog(s) will be used therapeutically or prophylactically, the duration of exposure of the recipient to the infectious bacteria, the size and weight of the individual, and other considerations within the scope of medical judgment. The duration for use of the composition containing the ACTH analog also depends on whether the use is for prophylactic purposes, wherein the use may be hourly, daily or weekly, for a short time period, or whether the use will be for therapeutic purposes wherein a more intensive regimen of the use of the composition may be needed, such that usage may last for hours, days or weeks, and/or on a daily basis, or at timed intervals during the day. Any dosage form employed should provide for a minimum number of units for a minimum amount of time. Dosages and desired drug concentrations of pharmaceutical compositions of the present invention may vary depending on the particular use envisioned. For example, where an ACTH analog of the invention is to be administered to a patient to treat a Cushing's Syndrome or premature labor, exemplary dosage amounts for an adult human include from about 0.001 to 100 mg/kg of body weight of active compound per day, which may be administered in a single dose or in the form of individual divided doses, such as from 1 to 4 times per day. It will be understood that the specific dose level and frequency of dosage for any particular compound may be varied and will depend upon a variety of factors including the activity of the specific compound employed, the metabolic stability and length of action of that compound, the species, age, body weight, general health, sex and diet of the patient, the mode and time of administration, rate of excretion, drug combination, and severity of the particular condition.

The determination of the appropriate dosage or route of administration is well within the skill of an ordinary physician. Animal-experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96. The concentration of the active units of ACTH analog that may provide for an effective amount or dosage of ACTH analog may be in the range of about 10 units/ml to about 500,000 units/ml of fluid in the wet or damp environment of the nasal and oral passages, and topically as well and possibly in the range of about 10, 20, 30, 40, 50, 60, 70, 80, 90, or 100 units/ml to about 50,000 units/ml. Representative values thus include about 200 units/ml, 300 units/ml, 500 units/ml, 1,000 units/ml, 2,500 units/ml, 5,000 units/ml, 10,000 units/ml, 20,000 units/ml, 30,000 units/ml, and 40,000 units/ml. More specifically, time exposure to the active ACTH analog units may influence the desired concentration of active ACTH analog units per ml. The formulations to be used for in vivo administration are preferably sterile. This is readily accomplished by filtration through sterile filtration membranes, prior to or following lyophilization and reconstitution. Therapeutic compositions herein generally are placed into a container having a sterile access port, for example, an intravenous solution bag or vial having a stopper pierceable by a hypodermic injection needle.

Examples of pharmaceutical compositions comprising ACTH analogs include injectable compositions, compositions providing for the sustained release of the ACTH analog over a desired time period, compositions for dermal administration, an injectable gel, coatings for an implantable medical devices, mucoadhesive compositions, or compositions for nasal or other inhalable compositions.

In some examples, an ACTH analog may be administered by intramuscular or intravenous injection. For example, the ACTH analogs can be administered intramuscularly, intravenously, subcutaneously, subdermally, intradermally or combinations thereof.

The injectable composition preferably comprises a suitable carrier and one or more ACTH analog compounds. The carrier may be comprised of distilled water, a saline solution, albumin, a serum, or any combinations thereof. In cases where intramuscular injection is the chosen mode of administration, an isotonic formulation may be used. Generally, additives for isotonicity can include sodium chloride, dextrose, mannitol, sorbitol and lactose. In some cases, isotonic solutions such as phosphate buffered saline are used. Stabilizers include gelatin and albumin. In some examples, a vasoconstriction agent is added to the formulation. The pharmaceutical preparations are provided sterile and pyrogen free. Generally, as noted above, intravenous injection may be most appropriate. Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, Glycerin or glycerol (1,2,3 propanetriol) is a commercially available carrier for pharmaceutical use. Glycerin or glycerol may be diluted in sterile water for injection, or sodium chloride injection, or other pharmaceutically acceptable aqueous injection fluid, and used in concentrations of 0.1 to 100% (v/v), 1.0 to 50% or about 20%. DMSO, is an aprotic solvent that can enhance penetration of many locally applied drugs. DMSO may be diluted in sterile water for injection, or sodium chloride injection, or other pharmaceutically acceptable aqueous injection fluid, and used in concentrations of 0.1 to 100% (v/v). The vehicle also may include Ringer's solution, a buffered solution, and dextrose solution, particularly when an intravenous solution is prepared.

Prior to, or at the time the ACTH analog is put in the carrier system, it may be desirable for the ACTH analogs be in a stabilizing buffer environment, maintaining a suitable pH range. The stabilizing buffer should allow for the optimum activity of the ACTH analog. The buffer may be a reducing reagent, such as dithiothreitol. The stabilizing buffer also may be or include a metal chelating reagent, such as ethylenediaminetetracetic acid disodium salt, or it also may contain a phosphate or citrate phosphate buffer. The buffers found in the carrier can serve to stabilize the environment for the ACTH analogs.

The carrier can optionally contain minor amounts of additives such as substances that enhance isotonicity and chemical stability. Such materials are non toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter ions such as sodium; non ionic surfactants such as polysorbates, poloxamers, or polyethylene glycol (PEG); and/or pharmaceutically acceptable salts, e.g., NaCl, KCl, $MgCl_2$, $CaCl_2$, and the like.

The term "pharmaceutically acceptable salts" refers to the relatively non-toxic, inorganic and organic acid addition salts of the inhibitor(s). These salts can be prepared in situ during the final isolation and purification of the inhibitor(s), or by separately reacting a purified inhibitor(s) in its free base form with a suitable organic or inorganic acid, and isolating the salt thus formed. Representative salts include the—14 hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, for example, Berge et al. (1977) "Pharmaceutical Salts", J. Pharm. Sci. 66:1-19.) In other cases, the inhibitors useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of an inhibitor(s). These salts can be likewise be prepared in situ during the final isolation and purification of the inhibitor(s), or by separately reacting the purified inhibitor(s) in its free acid form with a suitable base; such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Injectable pharmaceutical formulations comprising ACTH analogs can optionally include other therapeutic agents including antimicrobial agents, anti-inflammatory agents, antiviral agents, or local anesthetic agents. Local anesthetics include tetracaine, tetracaine hydrochloride, lidocaine, lidocaine hydrochloride, dyclonine, dyclonine hydrochloride, dimethisoquin hydrochloride, dibucaine, dibucaine hydrochloride, butambenpicrate, and pramoxine hydrochloride. An exemplary concentration for local anesthetics is about 0.025% to about 5% by weight of the total composition. Anesthetics such as benzocaine also may be used at a preferred concentration of about 2% to about 25% by weight.

Pharmaceutical compositions can also optionally comprise one or more additional bioactive agents to suppress the synthesis of steroid hormones at various levels (i.e. inhibitors of enzymes which catalyze various stages of the synthesis of steroid hormones), including the bioactive agents reviewed in J. Steroid Biochem., vol. 5, p. 501 (1974) which include the following: a) derivatives of diphenylmethane, e.g. amphenon B (which suppresses the synthesis of steroid hormones at stages 11-beta-, 17- and 21- of hydroxylase); b) derivatives of pyridine (SU-c series), e.g. metirapon (which suppresses synthesis at stage 11-beta of hydroxylase); c) substituted alpha, alpha-glutaramides, e.g. aminoglutetimide (which impedes the synthesis of pregnenolone from cholesterol through suppression of 20-alpha-hydroxylase and C20, C22-liase; d) steroid substances e.g. trilostan (3 beta-substituted steroid-3beta-hydroxy-5-androsten-17-one), which suppresses 3 beta-desoxysteroidhydrogenase-5.4-isomerase (Steroids, vol. 32, p. 257); e) steroids of the spironolactone family which are used as rapidly dissociating anti-Mineralocorticoids (PNAS USA 71(4) p. 1431-1435 (1974)); f) synthetic steroid described as an anti-Mineralocorticoids, ZK91587, showing specific binding properties for the kidney (Z. Naturforsch., 45b, p. 711-715 (1990)) and hippocampus type I MR (Life Science, 59, p. 511-21 (1996)), but not for type II GR. It may therefore be conveniently useful as a tool in the investigation of MR function in tissues containing both receptor systems.

ACTH analogs can be optionally administered with bioactive agents that specifically suppress the interaction of glucocorticoid hormones with hormone receptors include: a) Mifepriston (11β,17β)-11-[4-(Dimethylamino)phenyl]-17-hydroxy-17-(1-propynyl)estra-4,9-dien-3-one, which acts on receptors of glucocorticoid hormones to form a complex incapable of initiating mechanisms leading to glucocorticoid effect (Annals of New-York Academy of Science, vol. 761, p. 296-310 (1995)); said compound is also known as a contragestive agent (RU38486 or RU486); b) non-steroid substances (J:Steroid Biochem., vol. 31, p. 481-492 (1988)) e.g. drotaverina hydrochloride (a derivative of isoquinoline-1-(3.4-dietoxibene zilidene)-6.7-dietoxy-1,2,3,4-tetrahydrizoquinoline) or acetvisalicic acid (Moskovskava Meditsina, 1990, "Receptor mechanisms of the glucocorticoid effect" by V. P. Golikov). Antiglucocorticoids (e.g. Mifepristone) have been used in a clinical setting is to treat inoperable cases of nonpituitary Cushing's syndrome. In the case of Mifepristone (both an anti-progesterone and an anti-glucocorticoid), high doses (up to 800 mg per day) can be required. Employing a systematic application of strategies to increase activity and decrease cross-reactivity and undesirable side effects, impressive progress has been reported in the development of new antihormonal agents with greater potency and selectivity, especially in the antiestrogen and antiandrogen fields.

The effective dosage rates or amounts of the ACTH analog to be administered parenterally, and the duration of treatment will depend in part on the seriousness of the infection, the weight of the patient, the duration of exposure of the recipient to the infectious bacteria, the seriousness of the infection, and a variety of a number of other variables. The composition may be applied anywhere from once to several times a day, and may be applied for a short or long term period. The usage may last for days or weeks. Any dosage form employed should provide for a minimum number of units for a minimum amount of time. The concentration of the active units of ACTH analog believed to provide for an effective amount or dosage of ACTH analog may be in the range of about 10, 20, 30, 40, 50, 60, 70, 80, 90, or 100 units/ml to about 10,000,000 units/ml of composition, in a range of about 1000 units/ml to about 10,000,000 units/ml, and from about 10,000 to 10,000,000 units/ml. The amount of active units per ml and the duration of time of exposure depend on the nature of infection, and the amount of contact the carrier allows the ACTH analog to have. It is to be remembered that the ACTH analog works best when in a fluid environment. Hence, effectiveness of the ACTH analog is in part related to the amount of moisture trapped by the carrier. The concentration of the ACTH analog for the treatment is dependent upon the bacterial count in the blood and the blood volume.

When in vivo administration of an ACTH analog is employed, normal dosage amounts may vary from about 10 ng/kg to up to 100 mg/kg of subject body weight or more per day, or about 1 µg/kg/day to 10 mg/kg/day, depending upon the route of administration. Guidance as to particular dosages and methods of delivery is also provided below, as well as in the literature. It is anticipated that different formulations will be effective for different treatment compounds and different disorders, that administration targeting one organ or tissue, for example, may necessitate delivery in a manner different from that to another organ or tissue.

Pharmaceutical solutions for infusion or injection may be prepared in a conventional manner, e.g. with the addition of preservatives such as p-hydroxybenzoates or stabilizers such as alkali metal salts of ethylene diamine tetraacetic acid, which may then be transferred into fusion vessels, injection vials or ampules. Alternatively, the compound for injection may be lyophilized either with or without the other ingredients and be solubilized in a buffered solution or distilled water, as appropriate, at the time of use. Non aqueous vehicles such as fixed oils, liposomes, and ethyl oleate are also useful herein.

Additionally, a number of methods can be used to assist in transporting the ACTH analog across the cell membrane. The ACTH analog can be transported in a liposome, with the ACTH analog "inserted" in the liposomes by known techniques. Similarly, the ACTH analog may be in a reverse micelle. The ACTH analog can also be pegylated, attaching the polyethylene glycol to the non-active part of the ACTH analog. Alternatively, hydrophobic molecules can be used to transport the ACTH analog across the cell membrane. Finally, the glycosylation of the ACTH analog can be used to target specific internalization receptors on the membrane of the cell.

Materials having controlled release capability can be particularly desirable for certain methods of treatment. The ACTH analog can be combined with a carrier system such as a polymer that provides for sustained release of the ACTH analog compound over a desired period of time can be used. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

ACTH analog compounds can be combined with the sustained release carrier composition described by Loughman in U.S. Pat. No. 6,893,645, filed Jul. 15, 2002 and issued May 17, 2005, which is incorporated herein by reference. Other examples of sustained or controlled release formulations and methods that can be combined with ACTH analogs include Published U.S. Patent Application Nos. US2005/0164927A1, filed Aug. 18, 2004, by Cheung et al., US2003/0125528A1 filed Sep. 27, 2002 by Hay et al., US2003/0211966A1, filed Oct. 21, 2002 by Kubek et al. and US2003/0148938A1, filed Nov. 7, 2001 by Sharma et al., and US2003/0181361A1, filed Mar. 31, 2003 by Sharma et al., the disclosures of which are incorporated herein by reference in their entirety. In some embodiments, a controlled release treatment composition can include a controlled release polymer and an effective amount of an ACTH analog. The controlled release polymer can be a water swellable polymer, optionally including a desired level of cross linking moieties. The controlled release polymer can have a desired level of water solubility, or have minimal water solubility.

Polymer thickeners that may be used include those known to one skilled in the art, such as hydrophilic and hydroalcoholic gelling agents frequently used in the cosmetic and pharmaceutical industries. The hydrophilic or hydroalcoholic gelling agent can comprise, for example, "CARBOPOL®" (B.F. Goodrich, Cleveland, Ohio), "HYPAN®" (Kingston Technologies, Dayton, N.J.), "NATROSOL®" (Aqualon, Wilmington, Del.), "KLUCEL®" (Aqualon, Wilmington, Del.), or "STABILEZE®" (ISP Technologies, Wayne, N.J.). The gelling agent may comprise between about 0.2% to about 4% by weight of the composition. More particularly, an example of the compositional weight percent range for "CARBOPOL®" may be between about 0.5% to about 2%, while the weight percent range for "NATROSOL®" and "KLUCEL®" may be between about 0.5% to about 4%. A compositional weight percent range for both "HYPAN®" and "STABILEZE®" may be between about 0.5% to about 4%.

"CARBOPOL®" is one of numerous cross-linked acrylic acid polymers that are given the general adopted name carbomer. These polymers dissolve in water and form a clear or slightly hazy gel upon neutralization with a caustic material such as sodium hydroxide, potassium hydroxide, triethanolamine, or other amine bases. "KLUCEL®" is a cellulose polymer that is dispersed in water and forms a uniform gel upon complete hydration. Other gelling polymers include hydroxyethylcellulose, cellulose gum, MVE/MA decadiene crosspolymer, PVM/MA copolymer, or a combination thereof.

Preservatives also may be used in this invention and may comprise, for example, about 0.05% to 0.5% by weight of the total composition. The use of preservatives assures that if the product is microbially contaminated, the formulation will prevent or diminish microorganism growth. Some preservatives useful in this invention include methylparaben, propylparaben, butylparaben, chloroxylenol, sodium benzoate, DMDM Hydantoin, 3-Iodo-2-Propylbutyl carbamate, potassium sorbate, chlorhexidine digluconate, or a combination thereof.

Where sustained-release administration of an ACTH analog is desired in a formulation with release characteristics suitable for the treatment of any disease or disorder requiring administration of the ACTH analog, microencapsulation of the ACTH analog is contemplated. Preferred microencapsulation compositions suitable for use with the ACTH analogs include those described in U.S. Pat. No. 6,475,507 (filed Nov. 6, 2000) to Pellet et al., and U.S. Pat. No. 6,911,218 (filed Apr. 20, 1999) to Ignatious et al., both of which are incorporated herein by reference in their entirety. Microencapsulation of recombinant proteins for sustained release has been successfully performed with human growth hormone (rhGH), interferon-(rhIFN-), interleukin-2, and MN rgp120. Johnson et al., Nat. Med., 2:795-799 (1996); Yasuda, Biomed. Ther., 27:1221-1223 (1993); Hora et al., Bio/Technology. 8:755-758 (1990); Cleland, "Design and Production of Single Immunization Vaccines Using Polylactide Polyglycolide Microsphere Systems." in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010.

Sustained or control release carriers can be "long" or "slow" release carriers (such as, for example, certain nasal sprays, polymers, or capsules) could possess or provide a lower concentration of active (ACTH analog) units per ml, but over a longer period of time, whereas a "short" or "fast" release carrier (such as, for example, a gargle) could possess or provide a high concentration of active (ACTH analog) units per ml, but over a shorter period of time. The amount of active units per ml and the duration of time of exposure depend on the nature of infection, whether treatment is to be prophylactic or therapeutic, and other variables. Thus, the number of dosages will be dependent upon the circumstances and can range from 1-4 times per day or more, with durations from one day to multiple weeks. Infections can occur in the skin and thus such compositions may be formulated for topical application as well, using well known vehicles such as those described in U.S. Pat. Nos. 6,056,954 and 6,056,955. Micelles and multi lamellar micelles also may be used to control the release of ACTH analog.

The sustained-release formulations of these proteins can use a bioabsorbable polymer, such as poly-lactic-coglycolic acid (PLGA) polymer due to its biocompatibility and wide range of biodegradable properties. The degradation products of. PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), Biodegradable Polymers as Drul: Delivery Systems (Marcel Dekker: New York, 1990), pp. 1-41.

In some examples, a therapeutic composition comprises a mucoadhesive sustained release formulation and an ACTH analog. The mucosal lining, as disclosed and described, includes, for example, the upper and lower respiratory tract, eye, buccal cavity, nose, rectum, vagina, periodontal pocket, intestines and colon. Orahesive® from E.R. Squibb & Co is an adhesive which is a combination of pectin, gelatin, and sodium carboxymethyl cellulose in a tacky hydrocarbon polymer, for adhering to the oral mucosa. However, such physical mixtures of hydrophilic and hydrophobic components eventually fall apart. In contrast, the hydrophilic and hydrophobic domains in the present disclosure produce an insoluble copolymer. U.S. Pat. No. 4,948,580, also incorporated by reference, describes a bioadhesive oral drug delivery system. The composition includes a freeze dried polymer mixture formed of the copolymer poly(methyl vinyl ether/maleic anhydride) and gelatin, dispersed in an ointment base, such as mineral oil containing dispersed polyethylene. U.S. Pat. No. 5,413,792 (incorporated herein by reference) discloses paste like preparations comprising (A) a paste like base comprising a polyorganosiloxane and a water soluble polymeric material which are may be present in a ratio by weight from 3:6 to 6:3, and (B) an active ingredient. U.S. Pat. No. 5,554,380 claims a solid or semisolid bioadherent orally ingestible drug delivery system containing a water in oil system having at least two phases. One phase comprises from about 25% to about 75% by volume of an internal hydrophilic phase and the other phase comprises from about 23% to about 75% by volume of an external hydrophobic phase, wherein the external hydrophobic phase is comprised of three components: (a) an emulsifier, (b) a glyceride ester, and (c) a wax material. U.S. Pat. No. 5,942,243 describes some representative release materials useful for administering antibacterial agents, which disclosure is incorporated by reference. The dosage forms of the compositions of this disclosure can be prepared by conventional methods.

Compositions comprising an ACTH analog may be administered by nasal sprays, nasal drops, nasal ointments, nasal washes, nasal injections, nasal packings, bronchial sprays and inhalers. When the ACTH analog(s) is introduced directly by use of nasal sprays, nasal drops, nasal ointments, nasal washes, nasal injections, nasal packing, bronchial sprays, oral sprays, and inhalers, the ACTH analog may be in a liquid or gel environment, with the liquid acting as the carrier. A dry anhydrous version of the modified ACTH analog may be administered by the inhaler and bronchial spray, although a liquid form of delivery also may be used. The nasal spray can be a long acting or timed release spray, and can be manufactured by means well known in the art. An inhalant also may be used, so that the ACTH analog may reach further down into the bronchial tract, including into the lungs. Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Compositions for dermal administration of an ACTH analog can be formulated using a carrier for delivering at least one ACTH analog to or through the skin. The mode of application for the ACTH analog includes a number of different types and combinations of carriers which include, but are not limited to an aqueous liquid, an alcohol base liquid, a water soluble gel, a lotion, an ointment, a nonaqueous liquid base, a mineral oil base, a blend of mineral oil and petrolatum, lanolin, liposomes, protein carriers such as serum albumin or gelatin, powdered cellulose carmel, and combinations thereof. A mode of delivery of the carrier containing the therapeutic agent includes, but is not limited to a smear, spray, a time-release pACTH, a liquid absorbed wipe, and combinations thereof. The ACTH analog may be applied to a bandage either directly or in one of the other carriers. The bandages may be sold damp or dry, wherein the ACTH analog is in a lyophilized form on the bandage. This method of application is most effective for the treatment of infected skin. The carriers of topical compositions may comprise semi-solid and gel-like vehicles that include a polymer thickener, water, preservatives, active surfactants or emulsifiers, antioxidants, sun screens, and a solvent or mixed solvent system. U.S. Pat. No. 5,863,560 (Osborne) discusses a number of different carrier combinations that can aid in the exposure of the skin to a medicament. Another composition for topical administration includes a topical carrier such as Plastibase (mineral oil gelled with polyethylene).

In one example, the invention comprises a dermatological composition having about 0.5% to 10% carbomer and about 0.5% to 10% of a pharmaceutical that exists in both a dissolved state and a micro particulate state. The dissolved pharmaceutical has the capacity to cross the stratum corneum, whereas the micro particulate pharmaceutical does not. Addition of an amine base, potassium, hydroxide solution, or sodium hydroxide solution completes the formation of the gel. More particularly, the pharmaceutical may include dapsone, an antimicrobial agent having anti-inflammatory properties. One exemplary ratio of micro particulate to dissolved dapsone is five or less.

In another example, the invention comprises about 1% carbomer, about 80-90% water, about 10% ethoxydiglycol, about 0.2% methylparaben, about 0.3% to 3.0% dapsone including both micro particulate dapsone and dissolved dapsone, and about 2% caustic material. More particularly, the carbomer may include "CARBOPOL® 980" and the caustic material may include sodium hydroxide solution.

Methods of Treatment

The ACTH analog Compounds can be used to treat a variety of ACTH-related conditions. Methods of treatment comprising administration of one or more ACTH analog compounds to reduce the rate of ACTH-induced adrenal hormone secretion, to mitigate the effects of high levels of ACTH in patients or to block excess ACTH while maintaining a tonic state of adrenal function. The ACTH analog compounds can be useful in treating diseases relating to levels of ACTH, such as conditions responsive to modulation of ACTH receptors (such as MC-2R). The ACTH analog compounds can be administered to treat conditions related to the regulation of ACTH levels, for example to decrease the effects of high levels of ACTH in patients while maintaining a tonic state of adrenal function.

The ACTH analog compositions are useful, for example, in treating ACTH-related conditions, such as Cushing's Syndrome, impaired immune response as a result of hypersecretion of corticosteroid, initiation of premature labor (for example, by the hypothalamus-pituitary-adrenal axis), and related conditions. In one aspect, various ACTH analogs are prepared and administered to a patient to assess in vivo cortisone induction.

ACTH analog compounds can be administered to treat ACTH-producing tumors in the pituitary gland, in combination with high resolution MR pituitary imaging. ACTH analog compounds can also be administered in combination with petrosal sinus sampling to establish pituitary-derived ACTH hyper-secretion, pre-operative pituitary tumor localization and lateralization (see Oldfield, E. W. et al., "Petrosal sinus sampling with and without corticotrophin-releasing hormone for the differential diagnosis of Cushing's syndrome," N Engl J. Med., 325:897-905 (1991); and Findling, J. W. et al., Endocrinol Metab Clin North Am., 30:729-47 (2001)). Although 70% of pituitary microaderiomas are successfully resected by transsphenoidal approaches, surgical "cure" rates for macroadenomas are achieved in only about a third of patients in specialized centers (Mampalam, T. J. et al., Ann Intern Med., 109:487-93 (1988)).

ACTH analog compounds can also be administered in tumor treatments, including in conjunction with treatment for ACTH hypersecretion, or in combination with pituitary-directed radiation to suppress tumor growth and hormonal levels. Radiation effects may not be manifest for several years, and are ultimately associated with pituitary damage and dysfunction in most patients (Brada, M. et al., "The long-term efficacy of conservative surgery and radiotherapy in the control of pituitary adenomas," Clin Endocrinol., 38:571-8 (1993)). Hypercortisolism, cortisol hypersecretion, may be completely resolved by adrenalectomy (surgical removal of one or both of the adrenal glands), but this approach does not suppress pituitary tumor growth, and is also associated with other co-morbidity (see Trainer, P. J. et al., "Cushing's syndrome: Therapy directed at the adrenal glands," Endocrinol Metab Clin North Am., 23:571-584 (1994)).

ACTH analog compounds can be administered in combination with medical therapy, such as co-administration of cyproheptadine, an anti-serotonin agent, used to suppress ACTH secretion but ultimate efficacy was poor, and its use has been discontinued (Krieger, D. T. et al., "Cyproheptadine-induced remission of Cushings disease," N Engl J. Med. 293:893-6 (1975)). Although the antifungal, ketoconazole, suppresses adrenal cortisol biosynthesis, the drug does not inhibit pituitary tumor growth or ACTH secretion, and idiosyncratic hepatic impairment limits its longterm use (see Sonino, N., "The use of ketoconazole as an inhibitor of steroid production," N Engl J. Med., 317:812-8 (1987)).

During pregnancy, CRH can be produced by the placenta and fetal membranes in substantial amounts during the third trimester of pregnancy (see Frim, D. M. et al., "Characterization and gestational regulation of corticotrophin-releasing hormone messenger RNA in human placenta," J Clin Invest., 82:287-292 (1988)), giving rise to an increase in CRH concentrations in maternal peripheral plasma, particularly after 30 weeks gestation (see Sasaki, A. et al., "Immunoreactive corticotropin-releasing hormone in human plasma during pregnancy, labor, and delivery," J Clin Endocrinol Metab., 64:224-229 (1987); and Goland, R. S. et al., "High levels of corticotropin-releasing hormone immunoreactivity in maternal and fetal plasma during pregnancy," J Clin Endocrinol Metab., 63:119-1204 (1986)). Recent studies have suggested that maternal plasma levels of CRH are elevated in women with preterm labor (see Wolfe, C. D. A. et al., "Plasma corticotrophin releasing factor (CRF) in abnormal pregnancy," Br J Obstet Gynaecol., 95:1003-1006 (1988); Warren, W. B. et al, "Elevated maternal plasma corticotropin-releasing hormone levels in pregnancies complicated by preterm labor," Am J Obstet. Gynecol., 166:1198-1207 (1992); and McLean, M. et al., "A placental clock controlling the length of human pregnancy," Nat. Med., 1:460-463 (1995)) and lower in those destined to give birth postterm (McLean et al., supra.).

ACTH analogs may be used in combination with tocolytic, or labor-preventing, drugs to postpone labor. Examples of tocolytic drugs include Ritodrine and Terbutaline, which are beta-sympathomimetic. However, in order to be effective, these drugs must generally be administered before the full onset of labor, and are of uncertain efficacy or safety if administered after labor has begun. Although tocolytic drugs are sometimes continuously administered at low levels to a pregnant woman, normally by infusion, during the duration of a high risk period of her pregnancy, normally between about twenty-eight and thirty-four weeks gestation (28-34 weeks), the drugs can have undesirable side effects upon renal function, respiratory function, heart rate and general body musculature tone. Dosages often must remain low, such as up to about 0.1 cc per hour of 1 mg/cc solution Terbutaline. The effectiveness of these low dosages in avoiding the onset of labor is inconsistent, and poorly quantified. Accordingly, there is a need for new treatments and methods for treating premature labor. More importantly, new treatments and methods for premature labor are needed that do not present undesirable side-effects.

In one embodiment, ACTH analog compositions can be administered to reduce biosynthesis of ACTH. This method of treatment can be used in combination with, or preferably instead of, the administration of pharmaceutical agents such as Metryapone. Preferably, ACTH analog compositions can be administered to treat incidence of Cushing's disease that develop during pregnancy, for example as described in: J. R. Lindsay and L. K. Nieman (2005) "The Hypothalamic-Pituitary-Adrenal Axis in Pregnancy: Challenges in Disease Detection and Treatment," Endocrine Reviews 26: 775-800).

Treatment for this condition, usually to prolong pregnancy or to prepare for delivery, can include administration of an ACTH polypeptide and/or Metryapone, which has been observed to be well tolerated without adverse effects on maternal hepatic function or fetal development. The patents can be administered metryapone to slow down the biosynthesis of ACTH. ACTH analog compositions are particularly preferred when the cause of the hypersecretion of corticosteroid is believed to be a result of the elevated levels of ACTH (presumably from a pituitary tumor in these women), for example as part of a strategy to decrease the synthesis of corticosteroid.

In another aspect, methods for treating veterinary subjects are provided, such as methods for decreasing stress hormones to benefit the health of agricultural and aquacultural species grown at high population densities. Compositions comprising one or more ACTH analog compounds can be administered in a method for decreasing stress hormones to benefit the health of agricultural and aquacultural species grown at high population densities.

EXAMPLES

The following examples are included to demonstrate preferred embodiments of the invention. It should be appreciated by those of skill in the art that the materials and techniques disclosed in the examples which follow represent materials techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Serum Corticosteroid Induction Assay (In Vivo)

ACTH analogs with reduced ACTH-mediated secretion of blood corticosteroid can be identified by performing an in vivo Serum Corticosteroid Induction Assay to measure the blood corticosteroid level in a subject after administration of the ACTH analog.

The in vivo Serum Corticosteroid Induction Assay was performed according the following method. First, two to three month-old male FVB/N mice from our colony, five per group, were injected intraperitoneally with dexamethasone (0.4 mg/0.1 ml PBS per mouse; Sigma, St. Louis, Mo.) to suppress their endogenous ACTH production. See Hajos, G T et al., "Studies of the potency of polypeptides with ACTH action by a new method based on continuous measurement of plasma corticosterone," Steroids Lipids Res 3:225-228 (1972), Costa, J L, et al., "Mutational analysis of evolutionarily conserved ACTH residues," Gen Comp Endocrinol, 136:12-16 (2004), and Karpac, J, et al., "Development, Maintenance, and Function of the Adrenal Gland in Early Postnatal Pro-opiomelanocortin Null Mutant Mice," Endocrinology (2005), published online ahead of print Feb. 24, 2005, all of which are incorporated herein by reference.

Second, ninety to one hundred twenty minutes later, the dexamethasone-suppressed mice were injected subcutaneously between the shoulder blades with either unmodified mACTH(1-24) or one of several ACTH analog peptide compounds (1 µg/0.1 mL PBS/0.5% BSA), or with vehicle alone (control) (0.1 mL PBS/0.5% BSA). The following ACTH analog peptide compounds were administered to separate mice: 1: murine ACTH1-24; 2: V26F,E30K; 3: P19W,K21E,Y23R; 4: E30K,P36R; 5: ALA19-24; 6: V26F,P36R; 7: P19W, K21E; 8: P19W,K21A,delY23; 9: P19W,K21A; 10: KRRP16-19RAAW (AT814) (SEQ ID NO:20).

Third, one hour later, blood was collected within less than 1 minute from a small incision in the tail, and serum was flash-frozen and stored at −80° C. until assayed. Serum corticosterone was determined by competitive radioimmunoassay ($^{125}$I RIA kit; ICN, Costa Mesa, Calif.) according to the manufacturer's recommendations. One microliter of serum was used per assay sample. Samples were run in duplicates. The results for the ACTH analog peptides described above are presented in the graph of FIG. 1, showing activity as a percentage of ACTH activity. These ACTH analogs showed less activity than native ACTH.

Example 2

Serum Corticosteroid Inhibition Assay (In Vivo)

ACTH analogs with reduced ACTH-mediated secretion of blood corticosteroid can be identified by performing an in vivo Serum Corticosteroid Inhibition Assay to test their ability to inhibit adrenal hormone production induced by unmodified ACTH. The blood corticosteroid level in a subject was measured after administration of an ACTH analog test compound in combination with a compound with known corticosteroid-induction activity, such as ACTH or another ACTH analog. The ACTH analog test compound can be administered before, concurrently with, or after the corticosteroid-producing compound.

The in vivo Serum Corticosteroid Inhibition Assay was performed according the following method. The ACTH analog test compounds, such as those showing low activities in Example 1, were tested for their abilities to inhibit adrenal hormone production induced by unmodified ACTH.

First, two to three month-old male FVB/N mice from our colony, five per group, were injected intraperitoneally with dexamethasone (0.4 mg/0.1 ml PBS per mouse; Sigma, St. Louis, Mo.) to suppress their endogenous ACTH production.

Second, ninety to one hundred twenty minutes later, animals were injected subcutaneously between the shoulder blades with wild type ACTH and/or test ACTH analog peptides (1 µg/0.1 mL PBS/0.5% BSA) or with vehicle alone (0.1 mL PBS/0.5% BSA).

Third, one hour later, blood was collected within less than 1 minute from a small incision in the tail, and serum was flash-frozen and stored at −80° C. until assayed. Serum corticosterone was determined by competitive radioimmunoassay ($^{125}$I RIA kit; ICN, Costa Mesa, Calif.) according to the manufacturer's recommendations. One microliter of serum was used per assay sample. Samples were run in duplicates.

Results are shown graphically in FIG. 2, as described above, for the analog AT814 (SEQ ID NO:20). Potency of peptides is expressed as percent induction of corticosterone, with native mouse ACTH being 100%. Comparison of corticosterone induction 1 hour after the last peptide injection showed that AT814 reduces corticosterone induction to 35% of that of wildtype ACTH when applied 30 minutes before the ACTH injection, and to 10% of that of wildtype ACTH when applied at the same time as the ACTH injection.

Example 3

Adrenal Binding Assays (In Vitro)

ACTH analogs with the ability to bind adrenal receptors can be identified by performing an in vitro Adrenal Binding Assay. The amount of a radiolabelled ACTH analog test compound binding to explanted adrenal membrane can be measured to identify ACTH analogs with adrenal receptor binding activity. Preferably this is performed in a serum free medium (in vitro Serum-free Adrenal Binding Assay)

ACTH analogs with the ability to bind adrenal receptors with a greater affinity than compounds with known adrenal binding activity (preferably ACTH) can also be identified by performing an in vitro Adrenal Competitive Binding Assay, whereby measurement of the reduction in the amount of the radiolabelled adrenal-binding compound (e.g., ACTH) is measured at various concentrations of non-radio-labeled ACTH analog test compound in a medium containing explanted adrenal membrane. The reduction in adrenal membrane binding by the radio-labelled adrenal binding compound can be used to identify and characterize the binding activity of the ACTH analog test compound. In a series of in vitro Adrenal Competitive Binding assays, the reduction in binding by radio-labelled ACTH was measured in combination with addition of an ACTH analog test compound to the adrenal membrane medium.

The in vitro Serum-free Adrenal Competitive Binding Assay was performed according the following method. First, adrenals were removed from mice, dissected free of fat, and cut in half. See Costa, J L, et al., "Mutational analysis of evolutionarily conserved ACTH residues," *Gen Comp Endocrinol.* 136:12-16 (2004); and Weber, M M, et al., "Postnatal overexpression of insulin-like growth factor II in transgenic mice is associated with adrenocortical hyperplasia and enhanced steroidogenesis," *Endocrinology* 140:1537-1543 (1999), incorporated herein by reference.

Second, each adrenal half was placed into an individual well of a 4-well dish, one dish per mouse. Adrenal halves were incubated at 5% CO2, 37° C., in 0.5 ml serum-free medium (M199; Invitrogen) for 30 minutes to equilibrate.

Third, the adrenal halves were macerated or otherwise dissociated using Dounce Homogenizer to form a membrane fraction. The fraction was re-suspended in suitable buffer (Tris or HEPES). $^{125}$I Radio-labelled ACTH (200 ml) and non-radiolabelled test compound (e.g., ACTH, or an ACTH analog such as AT814 (SEQ ID NO:20)) were then added to the re-suspended membrane fraction in an amount to provide a total concentration of 0 nM, 10 nM, 100 nM and 1000 nM of the test compound; controls had no peptides added. The membrane fraction is recovered and radio signal was detected using a gamma detector. Reduction in the radio-signal detected after addition of the non-radiolabelled test compounds can be correlated to binding affinity of the various test compounds. A reduction in the radio-signal after addition of ACTH analog peptide test compounds can indicate an increased affinity for binding to adrenal ACTH receptors such as MC-2R, and the ability to displace ACTH at the adrenal MC-2R receptor.

FIG. 3 displays the results of a series of in vitro Serum-free Adrenal Competitive Binding Assays.

Example 4

Adrenal Inhibition Assay (In Vitro)

ACTH analogs that reduce or block the ACTH-mediated secretion of corticosteroid from adrenal membrane can be identified by performing an in vitro Serum-free Corticosteroid Inhibition Assay to test their ability to inhibit adrenal hormone production induced by unmodified ACTH. The corticosteroid level in a serum free media was measured after adding an ACTH analog test compound in combination with a compound with known corticosteroid-induction activity, such as ACTH or another ACTH analog. The ACTH analog test compound can be added before, concurrently with, or after the corticosteroid-producing compound.

The in vitro Serum-free Adrenal Inhibition Assay was performed according the following method. First, adrenals were removed from mice, dissected free of fat, and cut in half. See Costa, J L, et al., "Mutational analysis of evolutionarily conserved ACTH residues," *Gen Comp Endocrinol.* 136:12-16 (2004); and Weber, M M, et al., "Postnatal overexpression of insulin-like growth factor II in transgenic mice is associated with adrenocortical hyperplasia and enhanced steroidogenesis," *Endocrinology* 140:1537-1543 (1999), incorporated herein by reference.

Second, each adrenal half was placed into an individual well of a 4-well dish, one dish per mouse. Adrenal halves were incubated at 5% CO2, 37° C., in 0.5 ml serum-free medium (M199; Invitrogen) for 30 minutes to equilibrate.

Third, medium was removed and replaced by 0.5 ml M199 containing ACTH, AT814, or both, at 100 ng/ml each; controls had no peptides added.

Fourth, after 2 hours of incubation, the medium was removed, pooled for all four halves from each mouse, and assayed by corticosterone using standard RIA methods. corticosterone was determined by competitive radioimmunoassay ($^{125}$I RIA kit; ICN, Costa Mesa, Calif.) according to the manufacturer's recommendations. One microliter of serum was used per assay sample. Samples were run in duplicates. FIG. 4 displays the results.

Example 5 (Predicted)

Therapeutic Veterinary Administration

Fish hatcheries face a number of challenges as the goal of maximizing the total tonnage of fish for commercial purposes is confounded by the effects of crowding, and the spread of infection. In these environments, fish attempt to manage chronic stress insults through the hypothalamus/pituitary/interrenal (HPI) axis. In these situations a rise in corticosteroid, is usually flowed by some level of mortality, a desensitization to corticosteroid and then a new steady-state with respect to population density. Ironically during these "adjustment" cycles an extended rise in corticosteroid levels lowers resistance to infection.

The HPI in hatchery fish can be modulated by the time release administration of an ACTH analog of the invention, such as time release administration from a silastic capsule implant in these fish. This buffering of the HPI axis should improve survival and may facilitate weight gain in hACTHery fish.

Fish implanted with either the ACTH analog of the invention, or ACTH alone, would be subjected to environmental conditions that activate the HPI axis (i.e. crowding, shifts in pH, built up of ammonia and nitrates). Two parameters that could be analyzed in these paradigms are mortality and change in weight. Such parameters will demonstrate whether the ACTH analog of the invention is effective in lowering corticosterone levels in fish.

What is claimed is:

1. A composition comprising an isolated ACTH analog peptide or pharmaceutically acceptable salt thereof, wherein said ACTH analog peptide consists of the formula:

A1-A2-A3-A4-A5-A6-A7-A8-A9-A10-A11-A12-A13-A14-A15-A16-A17-A18-A19-A20-A21-A22-A23-A24-Asn-A26-Ala-Glu-A29-A30-Ser-Ala-Glu-Ala-Phe-A36-Leu-Glu-Phe-R wherein:
A1 is Ser or D-Ser;
A2 is Tyr or D-Tyr;
A3 is Ser or D-Ser;
A4 is Met, D-Met or Nle;
A5 is Glu, D-Glu, Cys or Asp;
A6 is His or D-His;
A7 is Phe, D-Phe, D-p-iodo-Phe or D-1-napth-Ala;
A8 is Arg or D-Arg;
A9 is Trp or D-Trp;
A10 is Gly, Cys, Lys, Orn, Dab or Dpr;
A11 is Lys, D-Lys or Gly;
A12 is Pro or D-Pro;
A13 is Val or D-Val;
A14 is Gly;
A15 is Lys, Gly, Val, Leu, Ile, Nle, or an amino acid with an alkyl side chain;
A16 is Lys, Gly, Val, Leu, Ile, Nle, or an amino acid with an alkyl side chain;
A17 is Arg, Ala, Gly, Val, Leu, Ile, Nle, or an amino acid with an alkyl side chain;
A18 is Arg, Ala, Gly, Val, Leu, Ile, Nle, or an amino acid with an alkyl side chain;
A19 is Pro, Trp or Ala;
A20-A21-A22-A23-A24 is Val-Lys-Val-Tyr-Pro (SEQ ID NO: 18) or Ala-Ala-Ala-Ala-Ala (SEQ ID NO: 19);
A26 is Gly or Val;
A29 is Asp or Asn;
A30 is Glu;
A36 is Pro; and
R is OH or a pharmaceutically acceptable salt moiety; and wherein,
A16-A17-A18 does not include two adjacent amino acid residues selected from the group consisting of: Lys and Arg; and
the amino acid sequence at positions 25-39 is optionally deleted said ACTH analog peptide is not Ser-Tyr-Ser-Met-Glu-His-Phe-Arg-Trp-Gly-Lys-Pro-Val-Gly-Lys-Arg-Ala-Ala-Trp-Val-Lys-Val-Tyr-Pro-Ac (SEQ ID NO: 20).

2. The composition of claim 1 wherein A19 is Trp.

3. The composition of claim 1, wherein at least one of A17 and A18 is Ala and at least one of A17 and A18 is Arg A18.

4. The composition of claim 1, wherein the administration of said ACTH analog peptide in an in vivo Serum Corticosteroid Inhibition Assay reduces ACTH-induced corticosteroid secretion by at least 10%.

5. The composition of claim 1, wherein said ACTH analog peptide binds to and displaces a peptide of SEQ ID NO:2 from an adrenal membrane, where said peptide binding is measured by an in vitro Serum-free Adrenal Competitive Binding Assay.

6. The composition of claim 5, wherein said ACTH analog peptide binds to the MC-2R adrenal membrane with at least a 2-fold greater affinity than the peptide of SEQ ID NO:2.

7. The composition of claim 2, wherein said ACTH analog peptide reduces the ACTH induced production of corticosterone by an adrenal membrane in an in vitro Serum-free Adrenal Inhibition Assay.

8. The composition according to claim 1, wherein said ACTH analog peptide reduces the ACTH-induced production of corticosterone by an adrenal membrane in an in vitro Serum Corticosteroid Induction Assay by at least 10% as compared to the reduction of ACTH-induced production of corticosterone by an adrenal membrane in an in vitro Serum Corticosteroid Induction Assay by a composition comprising a peptide of SEQ ID NO:2.

9. The composition of claim 8, wherein A19 is Trp.

10. The composition of claim 8, wherein the amino acid sequence at positions 25-39 is deleted.

11. The composition of: claim 1, wherein:
A1 is Ser;
A2 is Tyr;
A3 is Ser;
A4 is Met;
A5 is Glu;
A6 is His;
A7 is Phe;
A8 is Arg;
A9 is Trp;
A10 is Gly;
A11 is Lys;
A12 is Pro;
A13 is Val;
A15 is Lys;
A16 is Lys or Arg;
A17 is Lys or Ala;
A18 is Lys or Ala.

12. The composition according to claim 11, wherein A19 is Trp.

13. The composition of claim 11, wherein at least one of A17 and A18 is Ala and at least one of A16, A17 and A18 is Arg.

14. The composition of claim 11, wherein the administration of said ACTH analog peptide in an in vivo Serum Corticosteroid Inhibition Assay reduces ACTH-induced corticosteroid secretion by at least 10%.

15. The composition of claim 11, wherein the amino acid sequence at positions 25-39 is deleted.

16. A method of manufacturing a medicament for treating an ACTH-related condition, comprising the step of combining an ACTH analog peptide according to claim 1 with a suitable carrier, wherein said ACTH-related condition is Cushing's Disease or premature labor.

17. The method of claim 16, wherein an elevated blood corticosteroid concentration is a symptom of said ACTH-related condition.

18. The method of claim 16, wherein said medicament is formulated for administration by injection, inhalation or transdermal absorption.

19. A method of manufacturing a medicament for treating an ACTH-related condition, comprising the step of combining an ACTH analog consisting of SEQ ID NO:20 with a suitable carrier, wherein said ACTH-related condition is Cushing's Disease or premature labor.

20. A method of treating an ACTH-related condition comprising the administration of the composition of claim 1 to a subject in need thereof, wherein said ACTH-related condition is Cushing's Disease or premature labor.

21. The method of claim 20, wherein said pharmaceutical composition is formulated for administration by injection, inhalation or transdermal absorption into a subject.

22. The method of claim 21, wherein said pharmaceutical composition is formulated for injection and wherein said method further comprises the step of injecting said pharmaceutical composition into said subject.

23. The method of claim 20, further comprising the step of measuring the blood corticosteroid level of said subject before administering said pharmaceutical composition.

24. The method of claim 22, wherein said pharmaceutical composition is injected subcutaneously or intravenously.

25. The method of claim 22, further comprising the step of administering a pharmaceutical agent to lower the corticosteroid blood level of said subject before injecting said pharmaceutical composition into said subject.

26. The method of claim 25, wherein said pharmaceutical agent to lower said corticosteroid blood level comprises dexamethasone.

27. The method of claim 20, wherein said subject is a human.

28. The method of claim 20, wherein said pharmaceutical composition comprises a sustained release composition.

29. A composition comprising an isolated ACTH analog peptide or pharmaceutically acceptable salt thereof, wherein said ACTH analog peptide consists of the formula:
Ser-Tyr-Ser-Met-Glu-His-Phe-Arg-Trp-Gly-Lys-Pro-Val-Gly-Lys-A16-A17-A18-A19-Val-Lys-Val-Tyr-Pro-Asn-Gly-Ala-Glu-Asp-Glu-Ser-Ala-Glu-Ala-Phe-Pro-Leu-Glu-Phe (SEQ ID NO: xx)
wherein:
A16 is Lys, Arg, Gly, Val, Leu, Ile, Nle, Gln, Asn, Glu, Asp or an amino acid with an alkyl side chain;
A17 is Lys, Arg, Ala, Gly, Val, Leu, Ile, Nle, Asn, Glu, Asp or an amino acid with an alkyl side chain;
A18 is Lys, Arg, Ala, Gly, Val, Leu, Ile, Nle, Asn, Glu, Asp or an amino acid with an alkyl side chain;
A19 is Pro or Trp; and
wherein,
the amino acid sequence at positions 16-18 does not include two adjacent amino acid residues selected from the group consisting of: Lys and Arg;
the amino acid sequence at positions 25-39 is optionally deleted; and
said ACTH analog peptide is not Ser-Tyr-Ser-Met-Glu-His-Phe-Arg-Trp-Gly-Lys-Pro-Val-Gly-Lys-Arg-Ala-Ala-Trp-Val-Lys-Val-Tyr-Pro-Ac (SEQ ID NO: 20).

30. The composition of claim 29 wherein A19 is Trp.

31. The composition of claim 30 wherein at least one of A17 and A18 is Ala and at least one of A16, A17 and A18 is Arg.

32. The composition of claim 29 wherein the amino acid sequence at positions 25-39 is deleted.

33. The composition of claim 32 wherein A19 is Trp.

34. The composition of claim 32 wherein at least one of A17 and A18 is Ala and at least one of A16, A17 and A18 is Arg.

35. A method of manufacturing a medicament for treating an ACTH-related condition, comprising the step of combining an ACTH analog peptide according to claim 29 with a suitable carrier, wherein said ACTH-related condition is Cushing's Disease or premature labor.

36. A method of treating an ACTH-related condition comprising the administration of the composition of claim 29 to a subject in need thereof, wherein said ACTH-related condition is Cushing's Disease or premature labor.

* * * * *

UNITED STATES PATENT AND TRADEMARK OFFICE
CERTIFICATE OF CORRECTION

PATENT NO.        : 7,919,577 B2                                    Page 1 of 1
APPLICATION NO.   : 11/666485
DATED             : April 5, 2011
INVENTOR(S)       : Miles B. Brennan et al.

It is certified that error appears in the above-identified patent and that said Letters Patent is hereby corrected as shown below:

In the Claims

In column 51, claim 29, line 24, after "(SEQ ID" replace "NO:xx)" with --NO:22)--.

Signed and Sealed this
Seventh Day of June, 2011

David J. Kappos
Director of the United States Patent and Trademark Office

UNITED STATES PATENT AND TRADEMARK OFFICE
CERTIFICATE OF CORRECTION

| | |
|---|---|
| PATENT NO. | : 7,919,577 B2 |
| APPLICATION NO. | : 11/666485 |
| DATED | : April 5, 2011 |
| INVENTOR(S) | : Miles B. Brennan et al. |

It is certified that error appears in the above-identified patent and that said Letters Patent is hereby corrected as shown below:

<u>In the Claims</u>

In column 50, claim 11, line 27, replace "A16 is Lys or Arg;" with --A16 is Lys;--.

In column 50, claim 11, line 28, replace "A17 is Lys or Ala;" with --A17 is Ala;--.

In column 50, claim 11, line 29, replace "A18 is Lys or Ala." with --A18 is Ala.--.

Signed and Sealed this
Twenty-ninth Day of November, 2011

David J. Kappos
*Director of the United States Patent and Trademark Office*